United States Patent
Raymond et al.

(10) Patent No.: US 7,594,888 B2
(45) Date of Patent: Sep. 29, 2009

(54) EXPANDABLE PORTS AND METHODS FOR MINIMALLY INVASIVE SURGERY

(75) Inventors: Douglas Raymond, Randolph, MA (US); Shinikequa White, Dorchester, MA (US); Richard Pellegrino, Upton, MA (US); Anthony Carlone, Bristol, RI (US); William Frasier, New Bedford, MA (US); Connie Marchek, Foxboro, MA (US); Brian Murphy, Quincy, MA (US); Stephen Connolly, Sharon, MA (US); Nicholas Pavento, Walpole, MA (US); Sara Dziedzic, Braintree, MA (US)

(73) Assignee: Depuy Spine, Inc., Raynham, MA (US)

( * ) Notice: Subject to any disclaimer, the term of this patent is extended or adjusted under 35 U.S.C. 154(b) by 126 days.

(21) Appl. No.: 11/255,784

(22) Filed: Oct. 21, 2005

(65) Prior Publication Data

US 2006/0106416 A1    May 18, 2006

Related U.S. Application Data

(60) Provisional application No. 60/623,161, filed on Oct. 29, 2004.

(51) Int. Cl.
*A61B 1/32* (2006.01)
(52) U.S. Cl. .................... 600/219; 600/215; 600/222
(58) Field of Classification Search ............... 600/136, 600/144, 184, 201, 208, 210, 214, 215, 219, 600/220, 222, 224, 221, 216; 604/104, 107, 604/174, 178; 606/108, 191, 198
See application file for complete search history.

(56) References Cited

U.S. PATENT DOCUMENTS

| | | | | |
|---|---|---|---|---|
| 1,796,072 | A * | 3/1931 | Baer | 600/219 |
| 2,313,164 | A * | 3/1943 | Nelson | 600/208 |
| 2,320,709 | A | 6/1943 | Arnesen | |
| 3,246,646 | A | 4/1966 | Murphy Jr. | |
| 3,522,799 | A | 8/1970 | Gauthier | |
| 3,782,370 | A * | 1/1974 | McDonald | 600/207 |
| 3,841,317 | A * | 10/1974 | Awais | 600/203 |
| 4,263,899 | A | 4/1981 | Burgin | |
| 4,686,966 | A | 8/1987 | Tsai | |
| 4,765,311 | A | 8/1988 | Kulik | |

(Continued)

FOREIGN PATENT DOCUMENTS

WO    199833431    8/1998

(Continued)

OTHER PUBLICATIONS

Wiltse el al., New Uses and Refinements of the Paraspinal Approach to the Lumbar Spine, Spine, 1988, vol. 13, No. 6.

*Primary Examiner*—Cris L Rodriguez
*Assistant Examiner*—Hao D Mai

(57) ABSTRACT

An expandable port for minimally invasive surgery includes a first section, a second section, and at least one intermediate section. The port is expandable from a closed configuration in which the first section is proximate the second section along at least a portion of a length of the first section to an expanded configuration in which the first section is spaced apart from the second section. The intermediate portion spans a gap between the first section and the second section when the port is in the expanded configuration.

4 Claims, 25 Drawing Sheets

U.S. PATENT DOCUMENTS

| | | | |
|---|---|---|---|
| 4,817,587 A | 4/1989 | Janese | |
| 4,862,891 A | 9/1989 | Smith | |
| 5,000,163 A | 3/1991 | Ray | |
| 5,052,372 A | 10/1991 | Shapiro | |
| 5,052,373 A | 10/1991 | Michelson | |
| 5,125,396 A | 6/1992 | Ray | |
| 5,158,543 A | 10/1992 | Lazarus | |
| 5,183,978 A | 2/1993 | Sheridan | |
| 5,231,973 A | 8/1993 | Dickie | |
| 5,429,121 A | 7/1995 | Gadelius | |
| 5,472,426 A | 12/1995 | Bonati | |
| 5,503,617 A | 4/1996 | Jako | |
| 5,505,690 A * | 4/1996 | Patton et al. | 600/210 |
| 5,520,610 A | 5/1996 | Giglio | |
| 5,688,223 A | 11/1997 | Rosendahl | |
| 5,728,046 A | 3/1998 | Mayer | |
| 5,762,629 A | 6/1998 | Kambin | |
| 5,792,044 A | 8/1998 | Foley | |
| 5,813,978 A | 9/1998 | Jako | |
| 5,928,139 A | 7/1999 | Koros | |
| 5,931,777 A | 8/1999 | Sava | |
| 5,944,658 A | 8/1999 | Koros | |
| 5,954,635 A | 9/1999 | Foley | |
| 5,967,972 A | 10/1999 | Santilli | |
| 5,976,146 A | 11/1999 | Ogawa | |
| 6,042,542 A | 3/2000 | Koros | |
| 6,048,309 A | 4/2000 | Flom | |
| 6,063,088 A | 5/2000 | Winslow | |
| 6,074,343 A | 6/2000 | Nathanson | |
| 6,139,493 A | 10/2000 | Koros | |
| 6,159,179 A | 12/2000 | Simonson | |
| 6,187,000 B1 | 2/2001 | Davison | |
| 6,206,862 B1 | 3/2001 | Giamanco | |
| 6,224,545 B1 | 5/2001 | Cocchia | |
| 6,241,659 B1 | 6/2001 | Bookwalter | |
| 6,277,094 B1 | 8/2001 | Schendel | |
| 6,354,995 B1 * | 3/2002 | Hoftman et al. | 600/219 |
| 6,364,832 B1 * | 4/2002 | Propp | 600/220 |
| 6,416,465 B2 | 7/2002 | Brau | |
| 6,432,048 B1 * | 8/2002 | Francois | 600/220 |
| 6,464,634 B1 | 10/2002 | Fraser | |
| 6,520,907 B1 | 2/2003 | Foley | |
| 6,530,883 B2 | 3/2003 | Bookwalter | |
| 6,692,434 B2 | 2/2004 | Ritland | |
| 6,902,530 B1 * | 6/2005 | Pianka | 600/220 |
| 6,916,330 B2 | 7/2005 | Simonson | |
| 6,945,933 B2 | 9/2005 | Branch | |
| 6,951,538 B2 | 10/2005 | Ritland | |
| 7,008,431 B2 | 3/2006 | Simonson | |
| 7,179,225 B2 * | 2/2007 | Shluzas et al. | 600/219 |
| 2002/0165433 A1 * | 11/2002 | Stihl | 600/196 |
| 2003/0069477 A1 * | 4/2003 | Raisman et al. | 600/220 |
| 2003/0191371 A1 * | 10/2003 | Smith et al. | 600/210 |
| 2005/0137461 A1 | 6/2005 | Marchek | |
| 2005/0159651 A1 * | 7/2005 | Raymond et al. | 600/213 |
| 2005/0215866 A1 | 9/2005 | Kim | |

FOREIGN PATENT DOCUMENTS

| | | |
|---|---|---|
| WO | WO 9833431 A1 * | 8/1998 |
| WO | 2001080725 | 1/2001 |

* cited by examiner

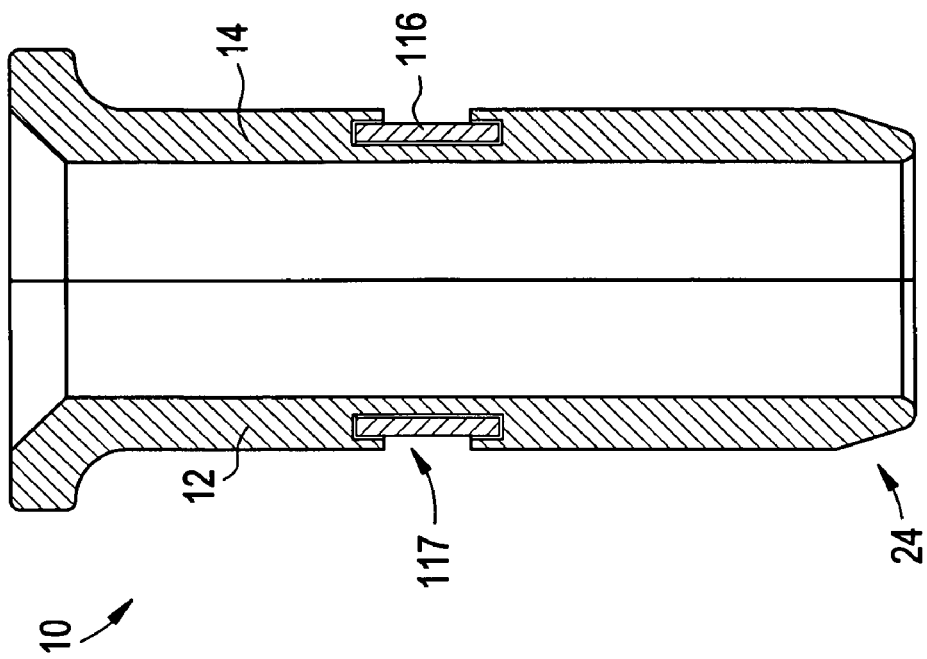
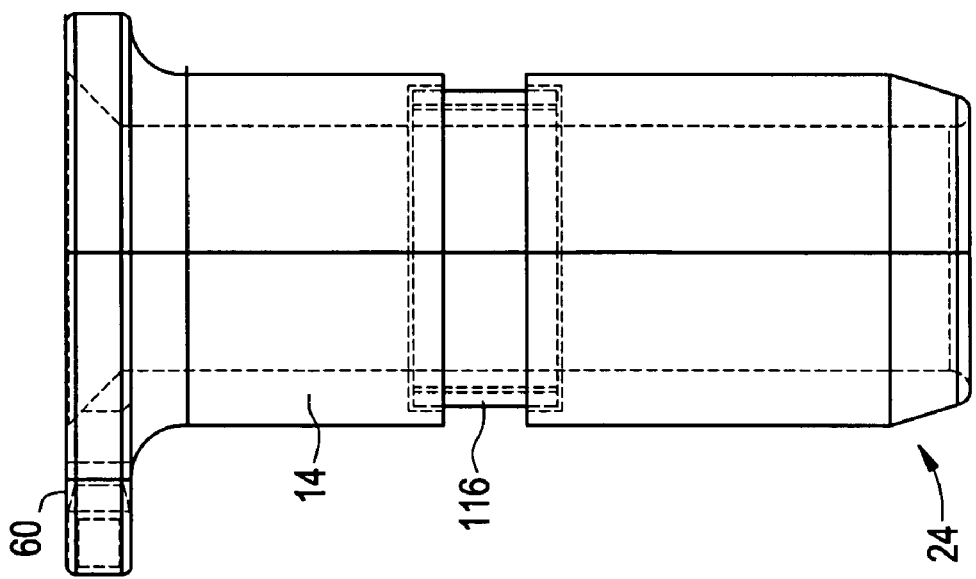

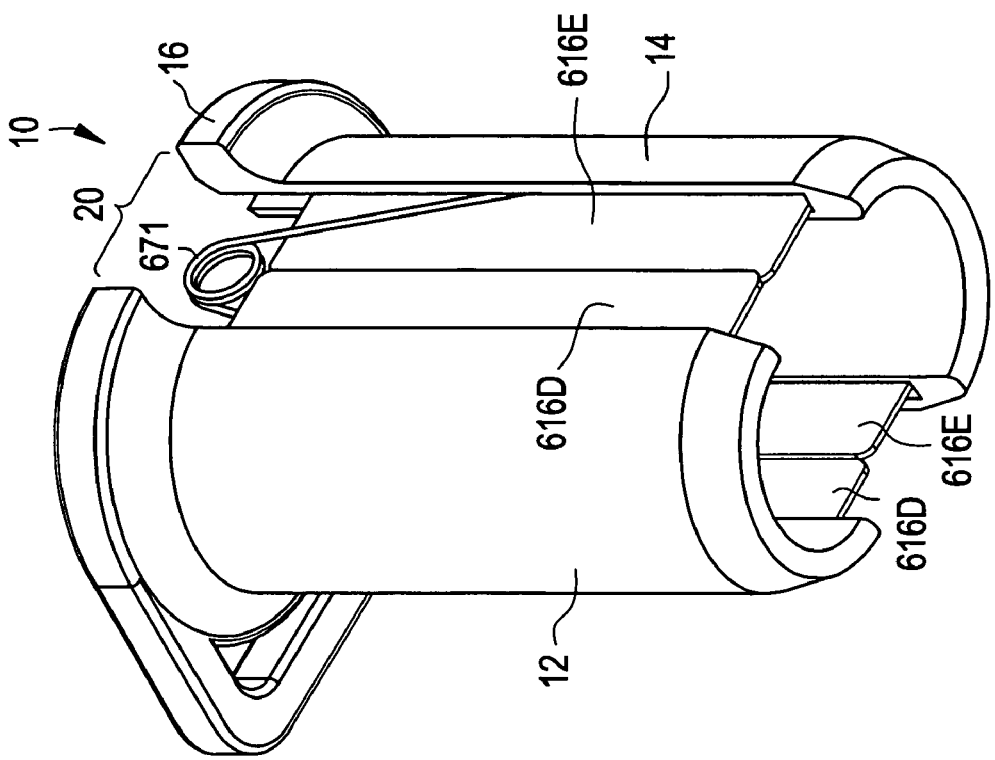
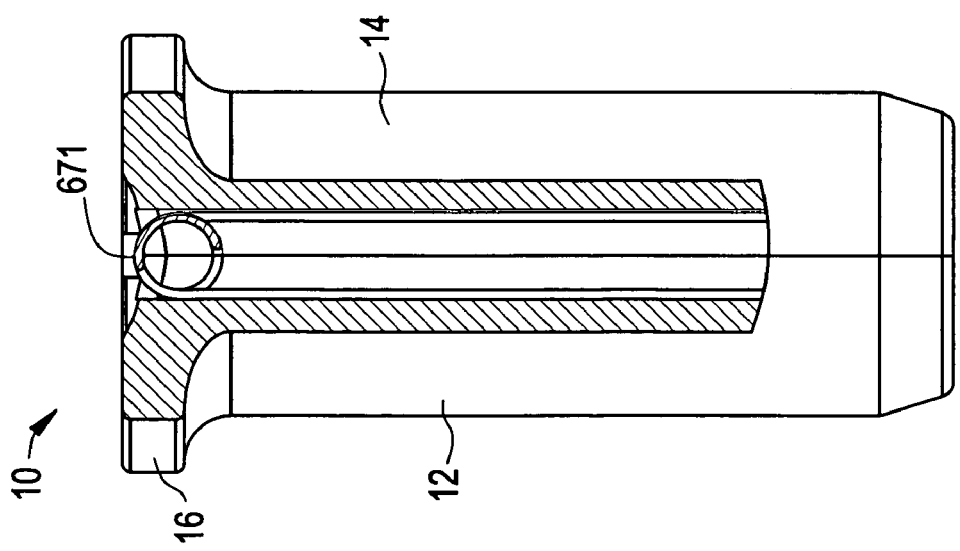

EXPANDABLE PORTS AND METHODS FOR MINIMALLY INVASIVE SURGERY

REFERENCE TO RELATED APPLICATIONS

This application claims priority to U.S. Provisional Patent Application No. 60/623,161, filed Oct. 29, 2004, which is incorporated herein by reference.

BACKGROUND

In surgical procedures, it is important to minimize trauma to the patient and damage to tissue to facilitate patient recovery. One way to accomplish this is to minimize the size of the incision for the surgical procedure. A number of retractors are available that are designed to expand a small surgical incision and provide access to a surgical site. Such retractors typically include two or more independent retractor blades that separate to expand the incision and create a working space in which to conduct the surgical procedure. One problem with such retractors is that retracted tissue often enters the space between the expanded retractor blades and interferes with access to the surgical site.

In addition to retractors, serial dilation may be used to expand a small incision to provide access to a surgical site. Typically, the surgical procedure is performed through a tubular shaped port that is positioned over the last inserted dilator. A problem with such ports is that the size and shape of the working space for the surgical procedure is limited due to the fixed geometry of the ports.

SUMMARY

Disclosed herein are expandable ports and methods of minimally invasive surgery that minimize tissue trauma and facilitate access to a surgical site. In one exemplary embodiment, an expandable port for minimally invasive surgery comprises a first section, a second section, and at least one intermediate section. The port may be expandable from a closed configuration in which the first section engages the second section along at least a portion of a length of the first section to an expanded configuration in which the first section is spaced apart from the second section. In the exemplary embodiment, the first section retains at least a portion of the intermediate section when the port is in the closed configuration. The intermediate portion, in the exemplary embodiment, spans a gap between the first section and the second section when the port is in the expanded configuration.

In another exemplary embodiment, an expandable port for minimally invasive surgery comprises an arcuate shaped first section, an arcuate shaped second section, a first intermediate section, and a second intermediate section. The port is expandable from a closed configuration in which the first section engages the second section along the length of the first section to an expanded configuration in which the first section is spaced apart from the second section. In the exemplary embodiment, the first section and the second section each house at least a portion of the first intermediate section and at least a portion of the second intermediate section when the port is in the closed configuration. In the exemplary embodiment, the first intermediate portion spans a first gap between the first section and the second section and the second intermediate portion spans a second gap between the first section and the second section when the port is in the expanded configuration.

In another exemplary embodiment, an expandable port for minimally invasive surgery comprises a first section, a second section and at least one intermediate section. In the exemplary embodiment, the port may be expandable from a closed configuration in which the first section is proximate the second section to an expanded configuration in which the first section is spaced apart from the second section. The at least one intermediate portion may span a gap between the first section and the second section when the port is in the expanded configuration.

An exemplary method of minimally invasive spine surgery comprises making an incision, positioning a port in the incision, and expanding the port along the length of the port by separating a first section of the port from a second section of the port along the length of the port. In the exemplary method, the expanded port provides a continuous pathway from the incision to a surgical site proximate the vertebra

BRIEF DESCRIPTION OF THE FIGURES

These and other features and advantages of the expandable ports and methods of minimally invasive surgery disclosed herein will be more fully understood by reference to the following detailed description in conjunction with the attached drawings in which like reference numerals refer to like elements through the different views. The drawings illustrate principles of the ports and methods disclosed herein and, although not to scale, show relative dimensions.

FIG. 11 is a side view of the expandable port of FIG. 10, illustrating the port in a closed position;

FIG. 12 is a cross sectional view of the expandable port of FIG. 10;

FIG. 26 is a side view of another exemplary embodiment of an expandable port, illustrating the port in a closed position;

FIG. 27 is a perspective view of the expandable port of FIG. 26, illustrating the port in an expanded position;

DETAIL DESCRIPTION

Figure 1:
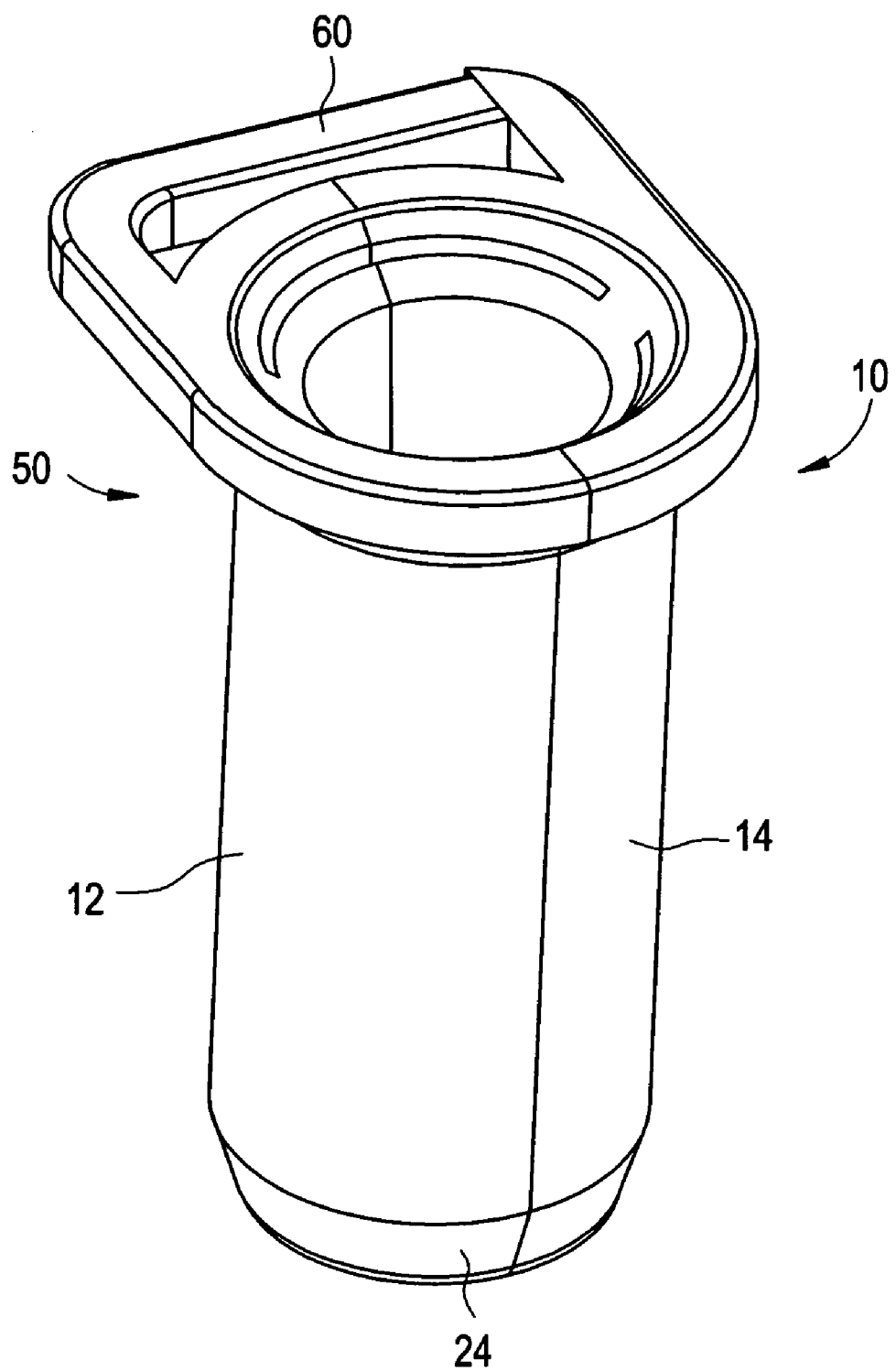
FIG. 1 is a front perspective view of an expandable port, illustrating the port in a closed configuration.
Figure 2:
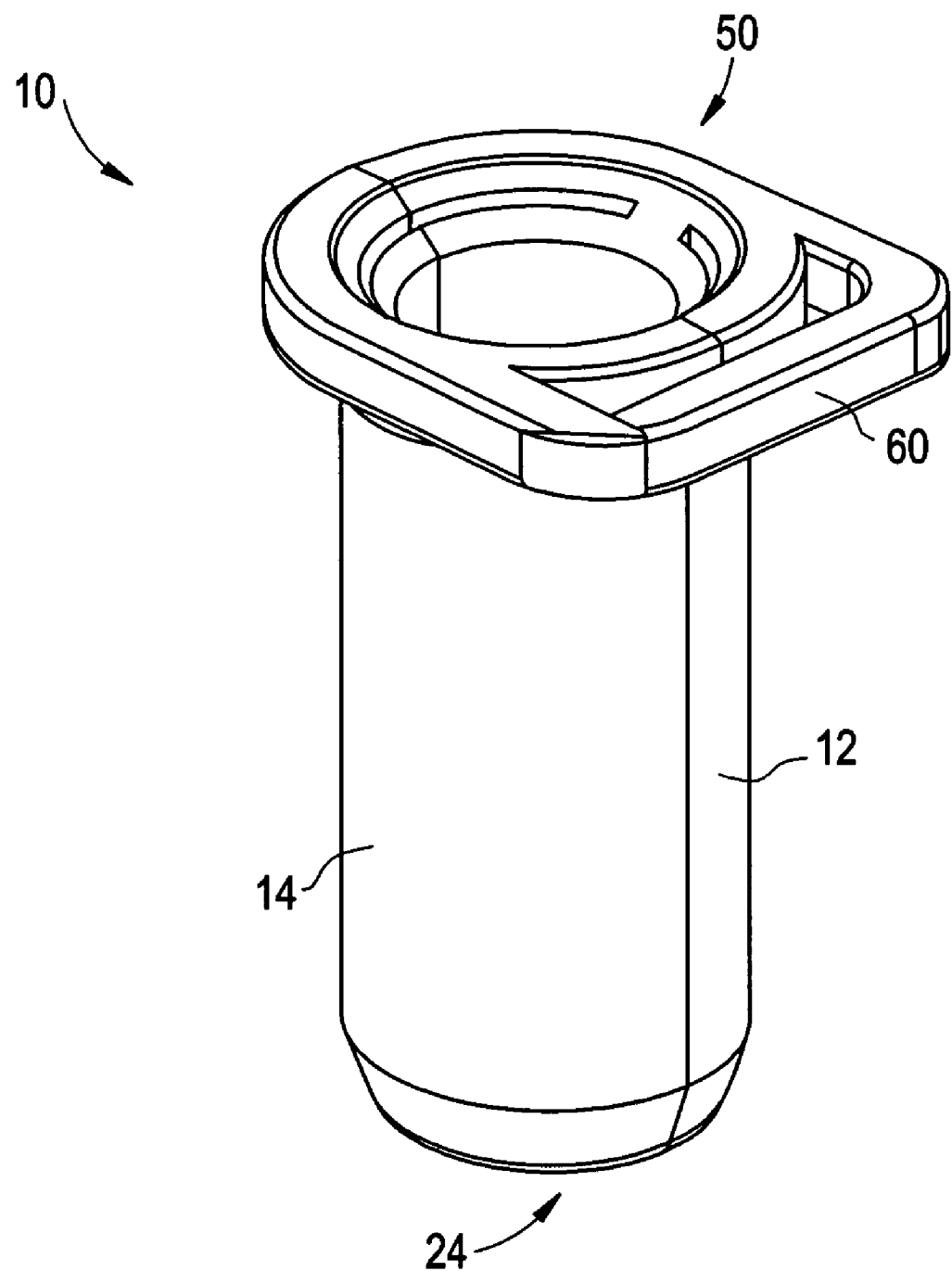
FIG. 2 is a rear perspective view of the expandable port of FIG. 1, illustrating the port in a closed configuration.
Figure 3:
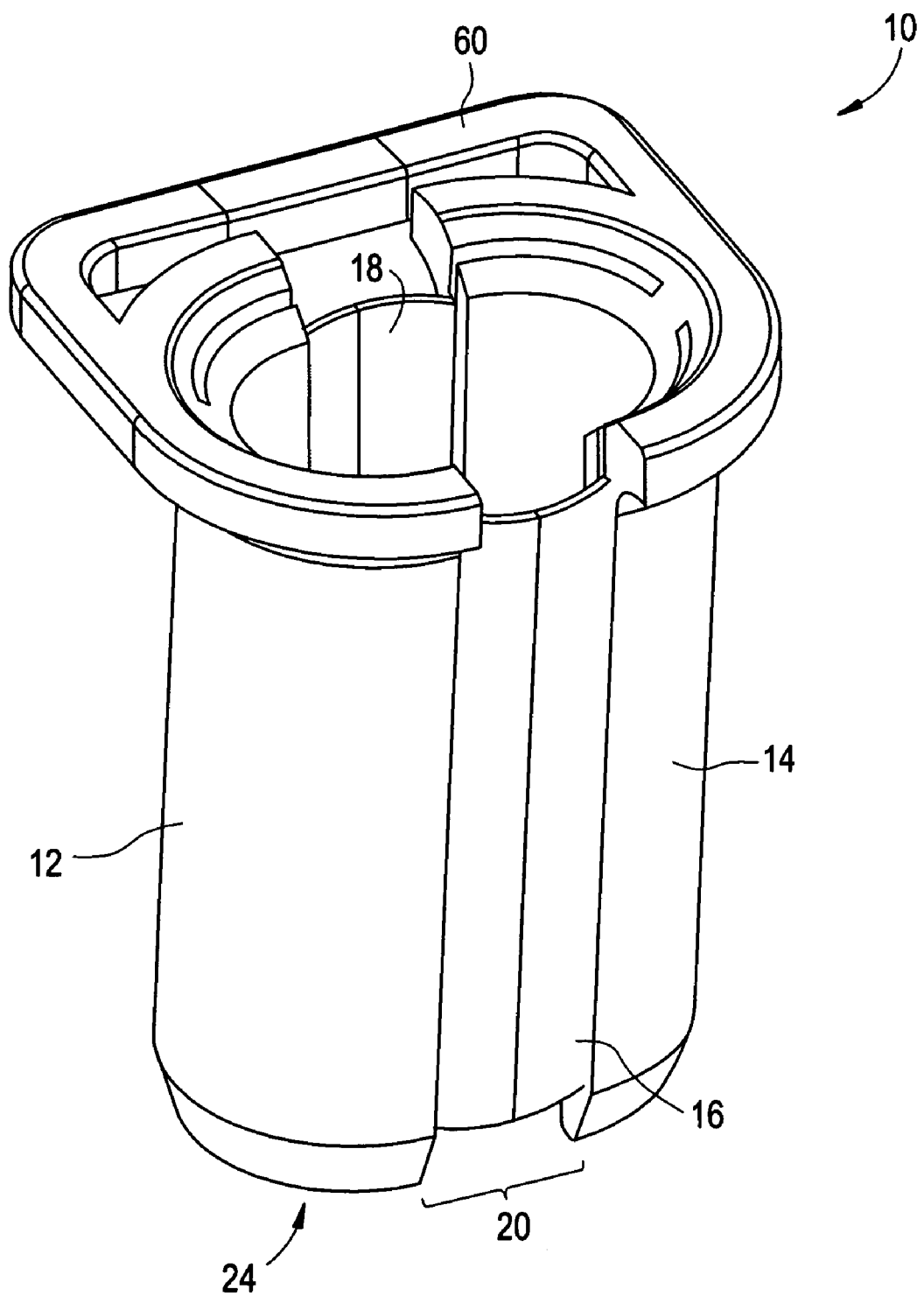
FIG. 3 is a front perspective view of the expandable port of FIG. 1, illustrating the port in an expanded configuration.
Figure 4:
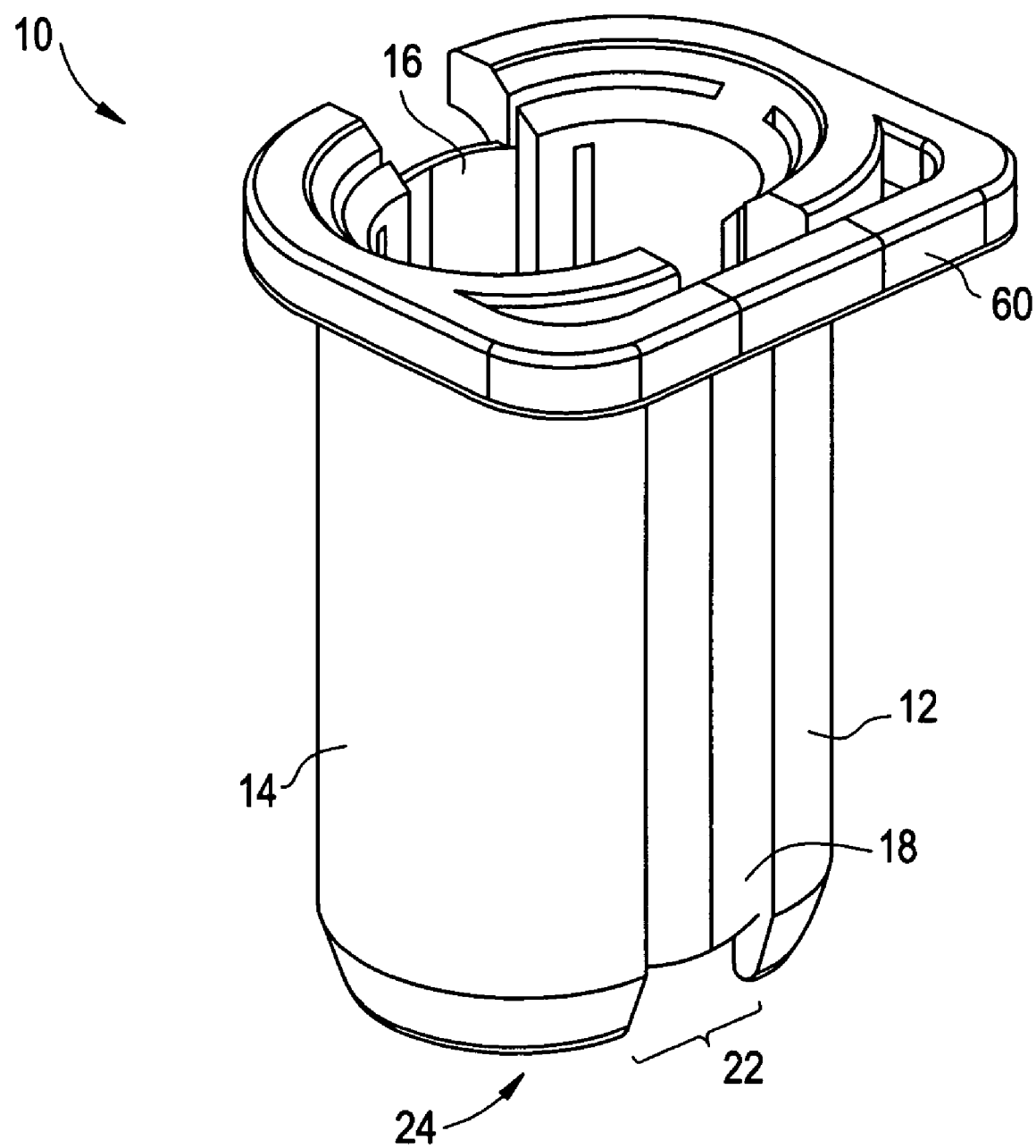
FIG. 4 is a rear perspective view of the expandable port of FIG. 1, illustrating the port in an expanded configuration.

Certain exemplary embodiments will now be described to provide an overall understanding of the principles of the structure, function, manufacture, and use of the expandable ports and methods of minimally invasive surgery disclosed herein. One or more examples of these embodiments are illustrated in the accompanying drawings. Those of ordinary skill in the art will understand that the expandable ports and methods of minimally invasive surgery specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

FIGS. 1-8 illustrate an exemplary embodiment of an expandable port 10 for use in minimally invasive surgery having a first section 12, a second section 14, and at least one intermediate section 16. In the exemplary embodiment, the expandable port 10 includes a first intermediate section 16 and a second intermediate section 18. The exemplary port 10 is expandable from a closed configuration, illustrated in FIGS. 1 and 2, which facilitates insertion of the port through an incision to a surgical site within the body, to an expanded configuration, illustrated in FIGS. 3-4, in which the port provides an expanded pathway to the surgical site. In the closed configuration, the first section 12 of the exemplary port 10 engages the second section 14 along at least a portion of the length of the first section 12. As discussed in more detail below, the first section 12 and/or the second section 14 may retain at least a portion of the intermediate section 16. For example, in the exemplary embodiment the first section 12 retains a portion of the first intermediate section 16 and a portion of the second intermediate section 18 and the second section 14 retains a portion of the first intermediate section 16 and a portion of the second intermediate section 18. In the expanded configuration, the first intermediate section 16 spans the gap between the first section 12 and the second section 14. For example, in the exemplary embodiment, the first intermediate section 16 spans a first gap 20 between the first section 12 and the second section 14 and the second intermediate section 16 spans a second gap 22 between the first section 12 and the second section 14.

The exemplary expandable port 10 may be used to provide access to a surgical site within the body and is particularly suited for use in spine surgery. For example, the exemplary port may be used to provide an expanded minimally invasive pathway from a skin incision to a surgical site proximate one or more vertebrae. The exemplary port may be used to provide access to all areas of the spine, e.g., the cervical spine, the thoracic spine, and the lumbar spine, through a variety of approaches to the spine, including, for example, posterior approaches, anterior approaches, and lateral approaches to the spine.

Figure 5:
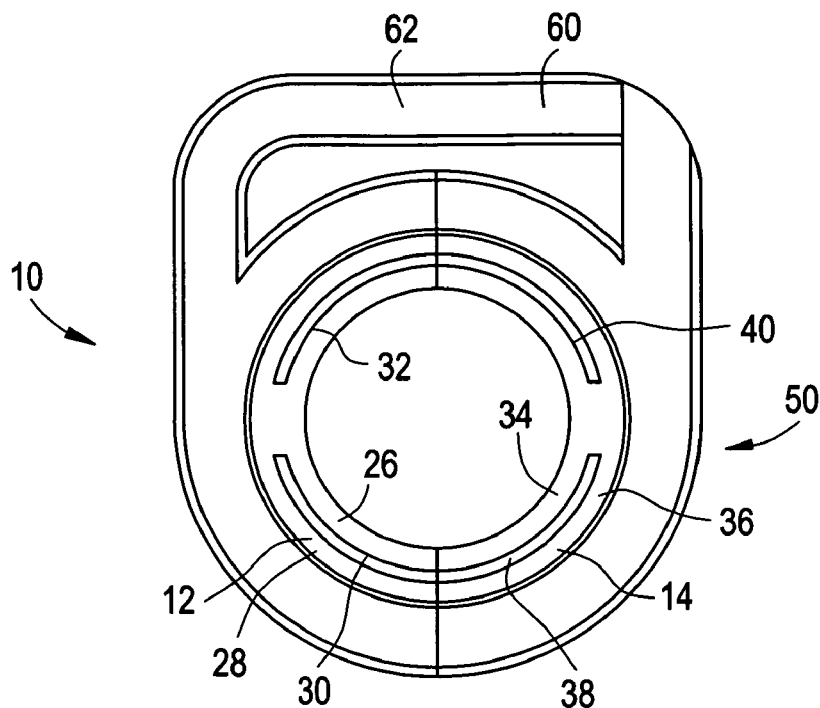
FIG. 5 is a top view of the expandable port of FIG. 1, illustrating the port in a closed configuration.

The exemplary port 10 may be sized and shaped to be inserted over one or more dilators employed to expand a minimally invasive incision. For example, the exemplary port 10 may have a size and shape corresponding to the size and shape of the dilator(s) over which the port 10 is inserted. In case of dilators having a circular cross section, for example, the exemplary port 10 may have a generally circular cross section in the closed configuration. In the case of oval shaped dilators, for example, the exemplary port 10 may have an oval cross section in the closed configuration. In the exemplary embodiment, the first section 12 of the exemplary port 10 may have an arcuate cross section and the second section 14 of the exemplary port 10 may have an arcuate cross section. The radius of curvature of the first section 12, in the exemplary embodiment, may be approximate to the radius of curvature of the second section 14 such that the exemplary port 10 has a generally circular cross section as illustrated in FIG. 5. The radius of curvature of the first section 12 may be approximate to or different from the radius of curvature of the second section 14 depending on the shape desired for the port 10.

In the illustrated exemplary embodiment, the exemplary port 10 includes two sections, the first section 12 and the second section 14. In other exemplary embodiments, the expandable port may have any number of additional sections. For example, in on exemplary embodiment, the expandable port may have three sections. In another exemplary embodiment, the port 10 may have four sections.

The length of the first section 12 of the exemplary port 10 and the length of the second section 14 of the exemplary port 10 may be selected based on the surgical procedure. For example, in the case of a posterior lumbar procedure, the length of the first section 12 and the length of the second section 14 may be selected to at least span from a posterior skin incision to proximate a lumbar vertebra. For example, in the case of an anterior cervical procedure, the length of the first section 12 and the length of the second section 14 may be selected to at least span from an anterior skin incision to proximate a cervical vertebra. In the exemplary embodiment, the length of the first section 12 may be approximate to the length of the second section 14. In alternative embodiments, the length of the first section 12 may be distinct from the length of the second section 14. For example, the length of the first section 12 may be less than the length of the second section 14 to provide the port 10 with a distal end 24 that conforms to the geometry of the anatomy against with the distal end 24 of the port is selected to engage. For example, the distal end 24 may have a sloped geometry or a stepped geometry to facilitate engagement with a portion of a vertebra. In the illustrated embodiment, the distal end 24 of the exemplary port 10 may be tapered to facilitate insertion of the exemplary port 10. In addition, the distal end 24 of the port 10 may include a contact surface having surface features that facilitates engagements with a portion of the vertebra. Such surface features may include, for example, surface roughening or teeth.

In the exemplary embodiment of the port 10, the first section 12 and/or the second section 14 may retain at least a portion of the intermediate section 16. The first section 12 of the exemplary port 10 may have an inner wall 26 and an outer wall 28. At least a portion of the inner wall 26 may be spaced apart from the outer wall 28 to define a housing for receiving at least portion of an intermediate section. For example, the inner wall 26, in the exemplary embodiment, is spaced apart from the outer wall 28 to define a first housing 30 for receiving a portion of the first intermediate section 16 and to define a second housing 32 for receiving a portion of the second intermediate section 18. Moreover, the inner wall 34 of the second section 14, in the exemplary embodiment, is spaced apart from the outer wall 36 of the second section 14 to define a third housing 38 for receiving a portion of the first intermediate section 16 and to define a fourth housing 40 for receiving a portion of the second intermediate section 18.

In the exemplary embodiment, the first housing 30 may be open on a first side 42 of the first section 12 that engages a third side 46 of the second section 14 and the third housing 38 may be open on the third side 46 of the second section 14. In this exemplary configuration, the first housing 30 communicates with the third housing 38 and the first intermediate section 16 may be positioned within the first housing 30 and the third housing 38 when the exemplary port 10 is in a closed configuration. For example, a portion of the first intermediate section 16 may be positioned within the first housing 30 and a portion of the first intermediate section 16 may be positioned within the third housing 38. The first housing 30 and the third housing 38 may be open at a proximal end of the exemplary port to facilitate positioning of the first intermediate section 16 within the first housing 30 and the third housing 38. The first housing 30 and the third housing 38 may be closed at the distal end 24 of the port 10 to maintain the first intermediate section 16 within the first housing 30 and the third housing 38.

Moreover, in the exemplary embodiment, the second housing 32 may be open on a second side 44 of the first section 12 that engages a fourth side 48 of the second section and the fourth housing 40 may be open on the fourth side 48 of the second section 14. In this exemplary configuration, the second housing 32 communicates with the fourth housing 40 and the second intermediate section 18 may be positioned within the second housing 32 and the fourth housing 40 when the exemplary port 10 in a closed configuration. For example, a portion of the second intermediate section 18 may be positioned within the second housing 32 and a portion of the intermediate section 18 may be positioned with the fourth housing 40. The second housing 32 and the fourth housing 40 may be open at the proximal end to facilitate positioning of the second intermediate section 18 within the second housing 32 and within the fourth housing 40. The second housing 32 and the fourth housing 40 may be closed at the distal end 24 of the port 10 to maintain the second intermediate section 18 within the second housing 32 and the fourth housing 40.

The size and shape of the first housing 30, second housing 32, third housing 38, and fourth housing 40 may be varied depending on, for example, the configuration of the port and the configuration of the intermediate section(s).

One skilled in the art will appreciate that the intermediate section(s) of the expandable port may be retained by the section(s) of the expandable port by retaining structures other than the housings described above. For example, the first section 12 and/or the second section 14 may include a retaining member provided on the inner surface of the first section 12 and/or second section 14 to retain an intermediate section. In certain exemplary embodiments, the first section 12 may include a proximal retaining member and a distal retaining member for retaining the intermediate section therebetween, for example, when the port is in the closed configuration. The retaining member may be, for example, a groove, lip, or other structure, in which a portion of the intermediate may rest when the port is in the closed configuration. In one exemplary embodiment, the first section 12 may include a proximal lip spaced apart from a distal lip and the intermediate section may engage the proximal lip and distal lip.

In certain alternative embodiments, the intermediate section(s) may not be retained by the sections of the port. For example, the intermediate section may be a separate component introduced to the port during or after expansion of the port 10 to span the gap between the sections of the port. In one exemplary embodiment, one or more intermediate sections may be configured to expand the port from a closed configuration. For example, the intermediate section may have a tapered distal end, e.g., tapering distally from a first extent to second narrower extent, to facilitate expansion of the port as the intermediate section is advanced distally relative to and between two sections of the port. The portion of the sections of the port receiving the intermediate section, e.g., one or more housings, may have an analogous taper at the proximal end thereof to facilitate expansion of the port.

The first section 12 and the second section 14 may be constructed from any material suitable for use in vivo, including, for example, metals, such as stainless steel or titanium, polymers, ceramics, or composites thereof.

In the exemplary embodiment, the first intermediate section 16 may be sized and shaped to span the first gap 20 between the first section 12 and the second section 14 and the second intermediate section 18 may be sized and shaped to span the second gap 22 between the first section 12 and the second section 14. The length of the first intermediate section 16 and the length of the second intermediate section 18 may be varied depending on, for example, the desired size and shape of the port in the expanded configuration. The first intermediate section 16 may have a length approximate to the length of the first section 12 and/or the length of the second section 14. The second intermediate section 18 may have a length approximate to the length of the first section 12 and/or the length of the second section 14. The first intermediate section 16 may have a length approximate to the length of the second intermediate section 18. For example, in the illustrated exemplary embodiment, the length of the first intermediate section 16 and the length of the second intermediate section 18 are each approximate to the lengths of the first section 12 and the second section 14. In such an embodiment, the first section 12, the second section 14, the first intermediate section 16, and the second intermediate section 18 cooperate to form an expanded port 10 that provides an expanded pathway from the proximal end 50 of the port 10 to the distal end 24 of the port 10 that is continuously enclosed by the port. In other exemplary embodiments, the first intermediate section 16 and the second intermediate section 18 may have lengths distinct from each other and from the first section 12 and the second section 14.

The intermediate section(s) may be constructed from any material suitable for use in vivo, including, for example, metals, such as stainless steel or titanium, polymers, ceramics, or composites thereof. The intermediate section(s) may be constructed from the same material as the first section 12 and the second section 14 or may be constructed from distinct materials.

Figure 6:
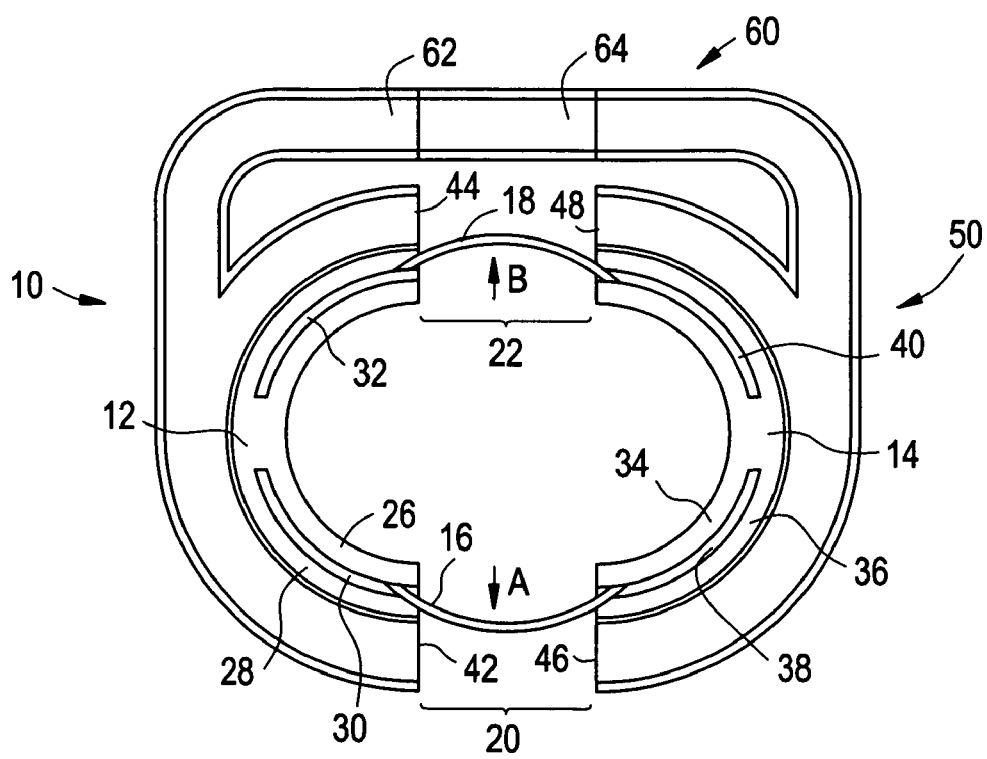
FIG. 6 is a top view of the expandable port of FIG. 1, illustrating the port in an expanded configuration.
Figure 7:
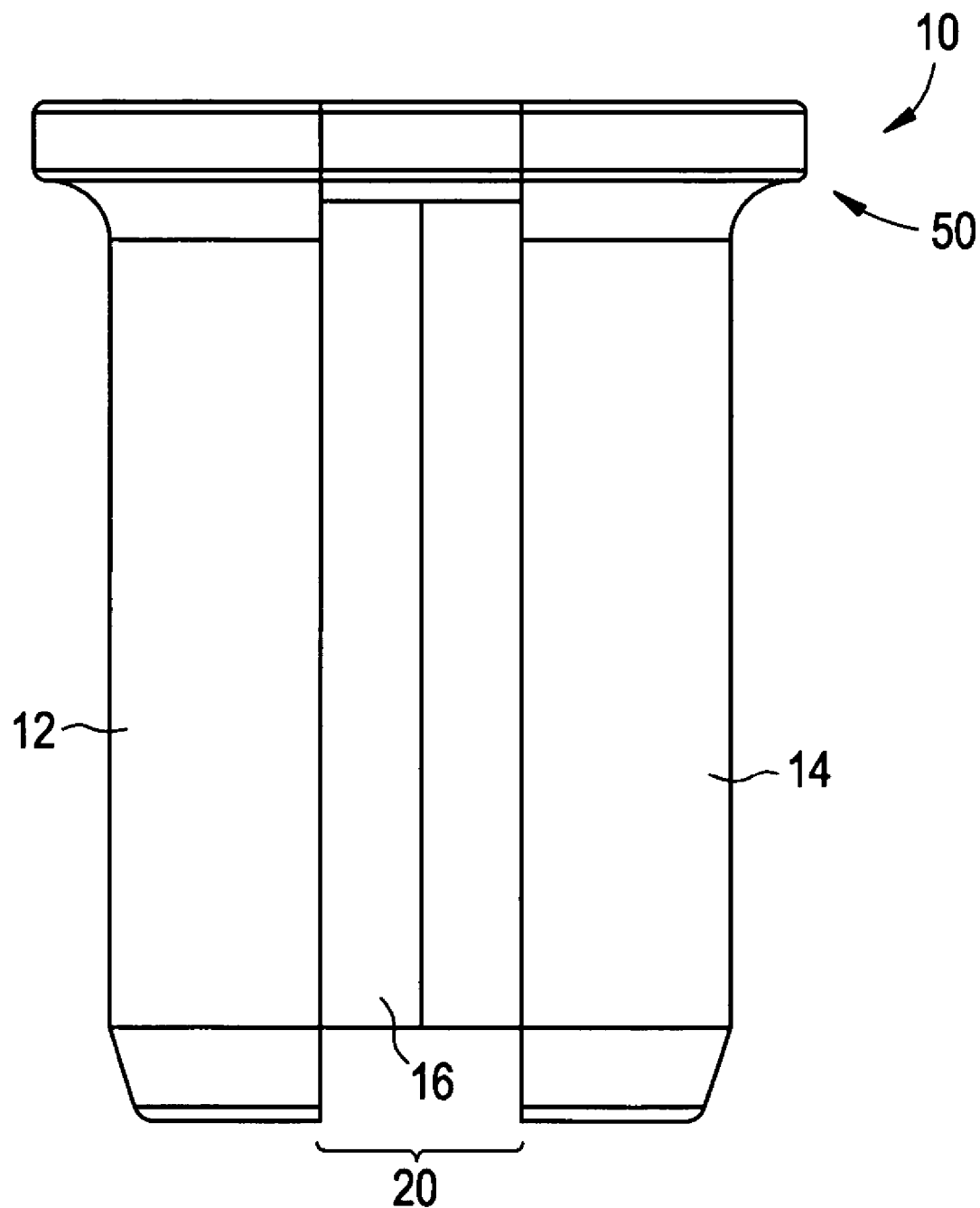
FIG. 7 is a front view of the expandable port of FIG. 1, illustrating the port in an expanded configuration.

In certain exemplary embodiments, one or more of the intermediate section(s) may be configured to expand when the expandable port 10 is expanded to the expanded configuration. For example, the first intermediate section 16 is configured to expand in a radially outward direction, indicated by arrow A in FIG. 6, when the port 10 is in an expanded configuration. Moreover, the second intermediate section 18 may be configured to expand in a radially outward direction, as indicated by Arrow B, when the port is in an expanded configuration. FIG. 6 illustrates the first intermediate section 16 in a radially outward expanded position and the second intermediate section 18 in a radially outward expanded position. The intermediate sections may be constructed of a resilient material, such as a metal or polymer, and may be biased to an expanded position. For example, the intermediate section may be biased to an expanded configuration have a first radius of curvature and may be retained in an un-expanded configuration having a second radius of curvature that is greater than the first radius when the port is in the closed configuration. In certain exemplary embodiments, the intermediate sections may be constructed of a shape memory alloy, such as, for example, nitinol.

The exemplary port 10 may have a handle 60 connected to the proximal end 50 of the port 10 to facilitate handling of the port 10 and to allow the handle to be attached to a support structure, such as an arm or the like, used to maintain the port in a desired position and orientation during use. The handle 60 may be configured to expand in connection with the expansion of the port 10. For example, in the illustrated embodiment, the handle 60 comprises a first handle section 62 that is connected to a proximal end of the first section 12 and a second handle section 64 that is connected to a proximal end of the second section 14. The first handle section 62 and the second handle section 64 may be adjustable relative to one another. In the illustrated embodiment, the first handle section 62 is telescopically adjustable relative to the second handle section 64 such that, for example, at least a portion of the second handle section 64 is received within the first handle section 62. Alternatively, a portion of the first handle section 62 may be received within the second handle section 64. The handle 60 may be provided with a locking mechanism to lock the port in a desired configuration, such as the expanded configuration or any position between the closed position and the expanded position. The locking mechanism may be a ratchet mechanism comprising, for example, a plurality of teeth provided on the second handle section 64 that are selectively engaged by a projection, for example, a pawl, provided on the first handle 62. Alternatively, a clamp or other locking mechanism may be employed.

Figure 8:
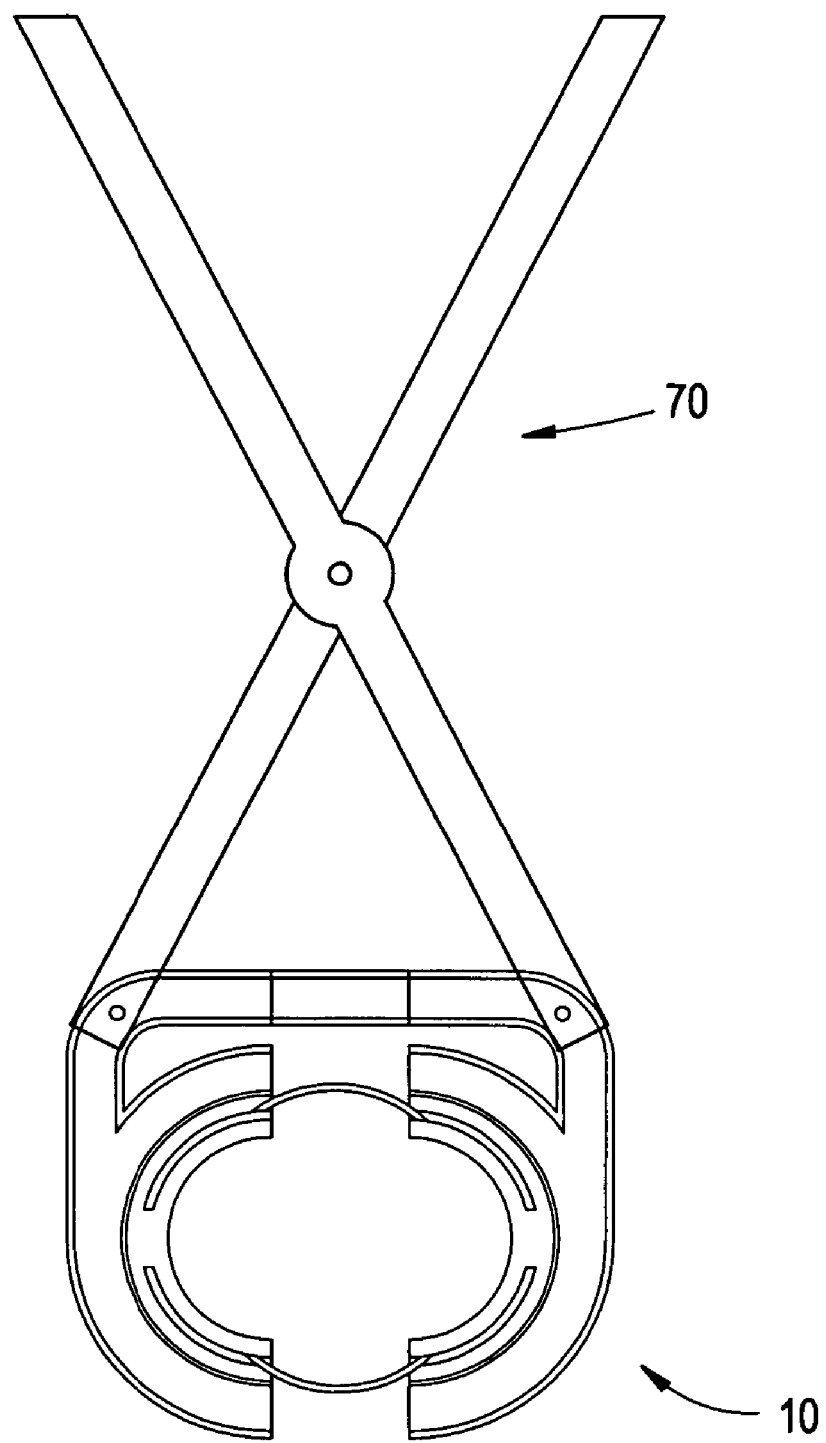
FIG. 8 is a top view of the expandable port of FIG. 1, illustrating an instrument for expanding the port.
Figure 9:
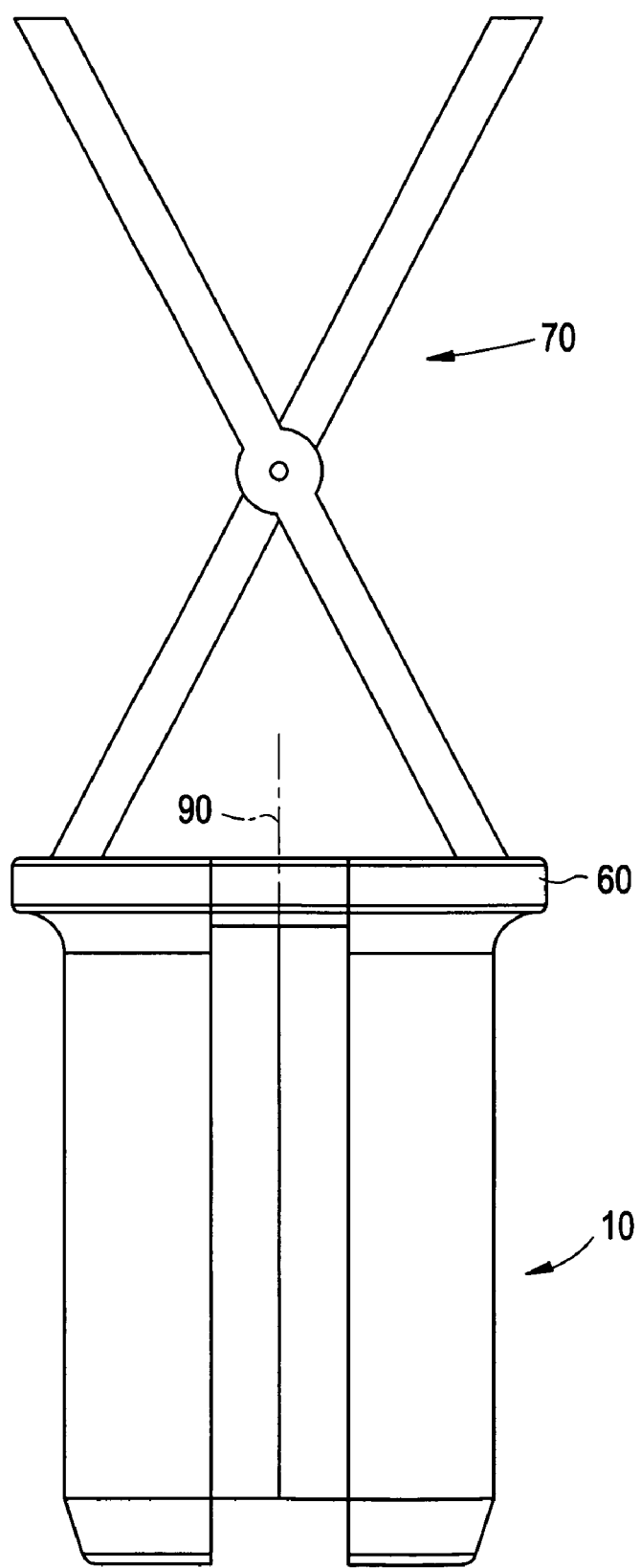
FIG. 9 is a front view of the expandable port of FIG. 1, illustrating an instrument for expanding the port.

In certain exemplary embodiments, an instrument 70 may be provided to expand the exemplary port 10 from the closed configuration to the expanded configuration. Referring to FIG. 8, for example, a scissor-like distraction instrument 70 is oriented perpendicular to the longitudinal axis of the port 10 and is coupled to the handle 60 of the port 10 in any conventional manner. The instrument 70 may be employed to expand the port 10 to the expanded configuration. The instrument 70 may be removed from the expandable port 10 once the port 10 is expanded. Alternatively, the instrument 70 may be an integral component of the handle 60. FIG. 9 illustrates the instrument 70 in an alternative arrangement in which the instrument is oriented parallel to the longitudinal axis 90 of the port 10. One skilled in the art will appreciate that instruments other than the exemplary scissor-like distraction instrument 70 may be used to expand the port 10.

In certain exemplary embodiments, the port 10 may be biased to an expanded configuration by providing one or more springs or the like between the sections of the port. In such an embodiment, a latch or other locking mechanism may be provided to retain the port in the closed configuration. Upon release of the latch, the port 10 may be expanded to the expanded configuration.

The expandable ports disclosed herein may be employed to provide surgical access to the spinal anatomy. In one exemplary embodiment, an expandable port, such as the exemplary expandable port 10, may be inserted, for example through an incision, into proximity to a vertebra of the spine and may be expanded to provide a pathway to the vertebra to facilitate performance of a surgical procedure proximate the vertebra. Exemplary procedures include laminotomy, facetectomy, foraminotomy, nerve root retraction, discectomy, and/or positioning of a spinal implant such as a spinal fixation element, such as a plate, rod, or tether, an interbody fusion device, a nucleus replacement device, an artificial disc, and a fastener, such as a bone anchor.

The incision may be a minimally invasive incision made in the patient's skin that is expanded, for example, by retraction and/or dilation, to create a pathway from the first incision to the proximate the vertebra. The incision may be expanded to create the pathway in any conventional manner. In certain embodiments, for example, the incision may be expanded by dilation to the desired size, shape, and orientation. For example, the incision may be sequentially dilated using a plurality of dilators to create the pathway to the vertebra. Exemplary methods and instruments for serial dilation are described in commonly owned U.S. Pat. No. 6,159,179, entitled Cannula and Sizing and Insertion Method; U.S. Patent Publication No. 2003-0083689 A1, entitled Non-Cannulated Dilators; and U.S. Patent Publication No. 2003-0083688 A1, filed Oct. 30, 2001, entitled Configured and Sized Cannulas, each of which is incorporated herein by reference. In other embodiments, a single dilator may be employed to expand the incision. Once dilation is concluded, the expandable port 10 may be positioned into the dilated incision over the dilator in the closed configuration. Alternatively, a retractor may be inserted into the dilated incision to further expand the incision and then the port may be positioned in the incision.

In certain exemplary embodiments, the incision may be expanded by inserting one or more retractors into the incision and expanding the incision to the desired size, shape, and orientation by expanding the retractor accordingly. Any type of conventional retractor or retractors may be employed to expand the incision. For example, suitable retractors are described in commonly owned U.S. Patent Publication No. 2005-0137461 A1, entitled Telescoping Blade Assemblies and Instruments for Adjusting an Adjustable Blade; U.S. Patent Publication No. 2005-0159651 A1, entitled Surgical Retractor Systems, Illuminated Cannula and Methods of Use; and U.S. Patent Publication No. 2005-0215866 A1, entitled Surgical Retractor Positioning Device, each of which are incorporated herein by reference.

In certain exemplary embodiments, the incision may be expanded to create a pathway by an intermuscular procedure that includes locating a muscle plane separating two muscles and separating the muscles at the muscle plane to create the first pathway. For example, in certain exemplary methods, the intermuscular plane separating the multifidus and longissimus muscles may be located through the incision. The multifidus and longissimus muscles may be separated at the muscle plane by blunt dissection, for example, by inserting a finger or an instrument, such as a retractor, through the muscle plane and advancing the finger or instrument to the vertebra to create the pathway to the vertebra. Intermuscular procedures are described in detailed in U.S. Pat. No. 6,692,434, entitled Method and Device for Retractor for Microsurgical Intermuscular Lumbar Arthrodesis; U.S. Patent Publication No. 2002-0123668 A1, entitled Retractor and Method for Spinal Pedicle Screw Placement; and *New Uses and Refinements of the Paraspinal Approach to the Lumbar Spine*, L. L. Wiltse and C. W. Spencer, Spine, Vol. 13, No. 6, Nov. 6, 1988, each of which is incorporated herein by reference.

The incision may be a percutaneous skin incision that has a shape and extent that is less than, equal to, or slightly greater than, the extent of the instruments and implants being inserted thereto. In certain exemplary embodiments, for example, the incision may be a stab incision that is expanded to facilitate positioning of the port 10 therethrough.

Once positioned in the incision, the port 10 may be expanded along the length of the port by separating the first section 12 of the port 10 from the second section 14 of the port 10 along the length of the port 10. As the port 10 is expanded, the first intermediate section 16 advances from the first section 12 and the second section 14 into the first gap 20 between the first section 12 and the second section 14 and the second intermediate section 18 advances from at the first section 12 and the second section 14 into the second gap 22 between the first section 12 and the second section 14. The expanded port 10 provides a pathway proximate to the vertebra that is continuously enclosed by the port 10 along the length of the port 10.

Figure 10:
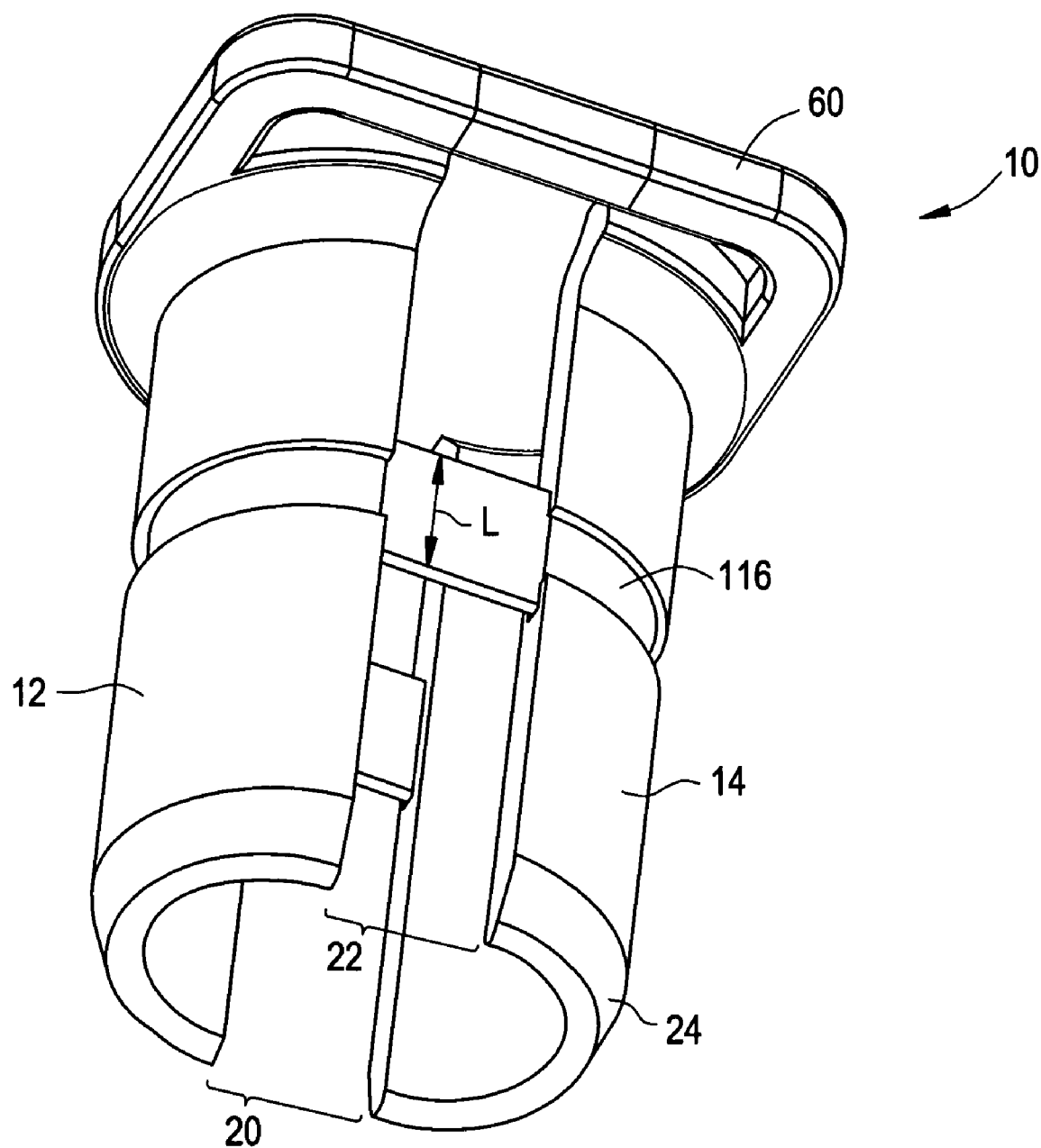
FIG. 10 is a perspective view of another exemplary embodiment of an expandable port, illustrating the port in an expanded position.

FIGS. 10-12 illustrate another exemplary embodiment of an expandable port 10 having a first section 12, a second section 14, and at least one expandable intermediate section. In the illustrated embodiment, the expandable intermediate section is an elastic member 116 that expands from a collapsed configuration, illustrated in FIGS. 11 and 12 to an expanded configuration, illustrated in FIG. 10, to span the gaps 20 and 22 between the first section 12 and the second section 14.

The elastic member 116 may have a shape corresponding to the cross sectional shape of the port 10. For example, the elastic member 116 may be generally circular or generally oval in shape. The elastic member 116 may be constructed from any elastic material, including natural and synthetic polymers, such as, for example, rubber. The length L of the elastic member 116 and the position of the elastic member 116 along the length of the port 10 may be varied. In the illustrated embodiment, for example, the length L of the elastic member 116 is less than the length of the first section 12 and the second section 14 and the elastic member 116 may be generally centrally located along the length of the port 10. In other embodiments, the elastic member 116 may have a length L substantially equal to the length of the first section 12 and/or second section 14. In other exemplary embodiments, the elastic member 116 may located approximate to the distal end 24 of the port 10 or approximate the proximal end of the port 10. Any number of elastic members 116 may be provided. For example, in certain exemplary embodiments, a plurality of elastic members 116 may be positioned along the length of the port 10, as illustrated FIGS. 13-15 discussed below.

The elastic member 116 may be positioned about the outer surface of the first section 12 and the second section 14. In the illustrated embodiment, the elastic member 116 may be positioned in a groove 117 provided in the outer surface of the first section 12 and the second section 14. The groove 117 may be sized and shape to retain the elastic member 116 relative to the port 10. In the illustrated embodiment, for example, the groove 117 has a generally C-shaped cross section to facilitate retention of the elastic member 116 relative to the port 10.

The elastic member 116 may bias the expandable port 10 to the closed position, illustrated in FIGS. 11 and 12. In such embodiments, the handle 60 may include a locking mechanism, discussed above, to lock the port in a desired configuration, for example, in the expanded position.

Figure 13:
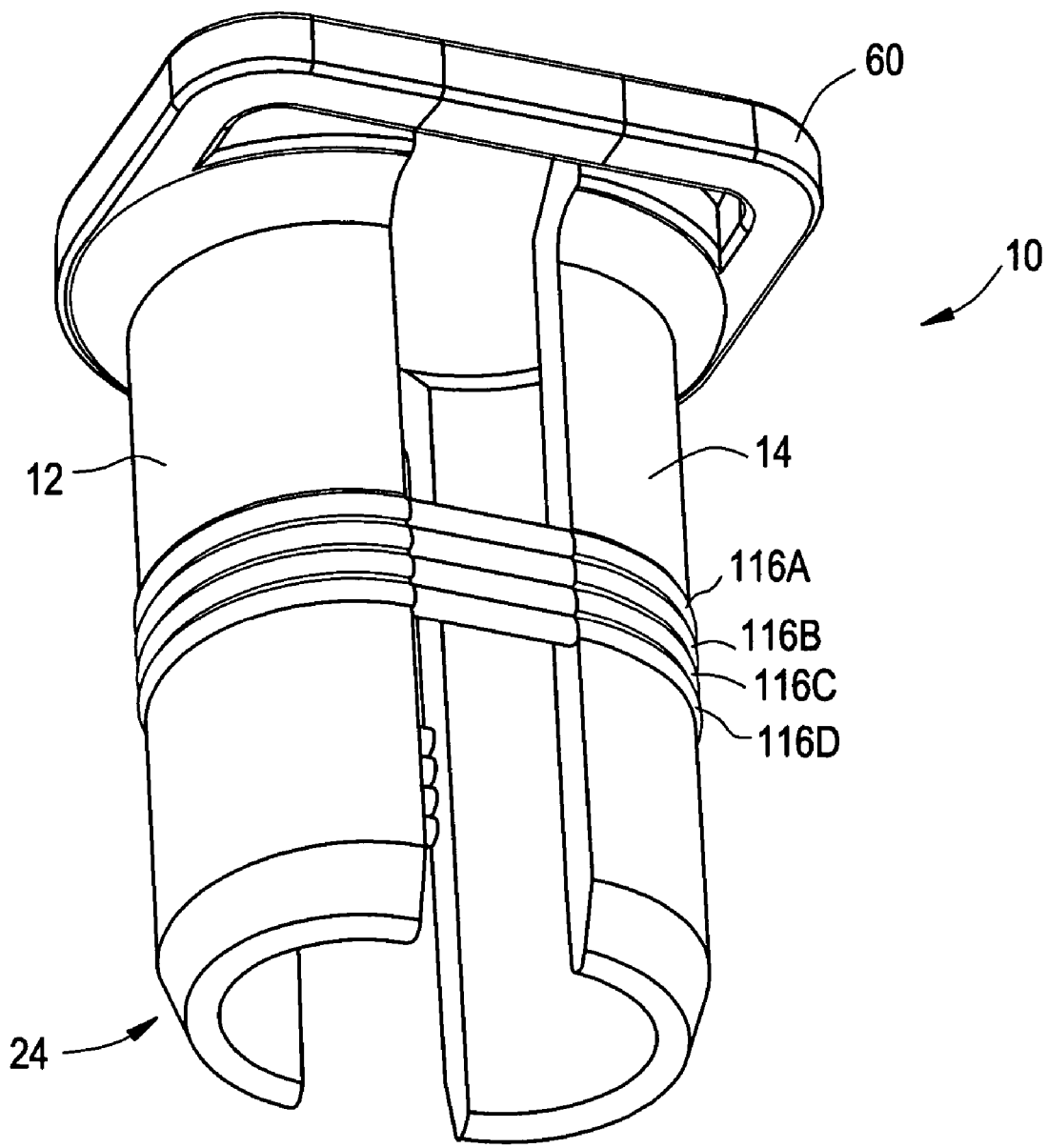
FIG. 13 is a perspective view of another exemplary embodiment of an expandable port, illustrating the port in an expanded position.
Figure 15:
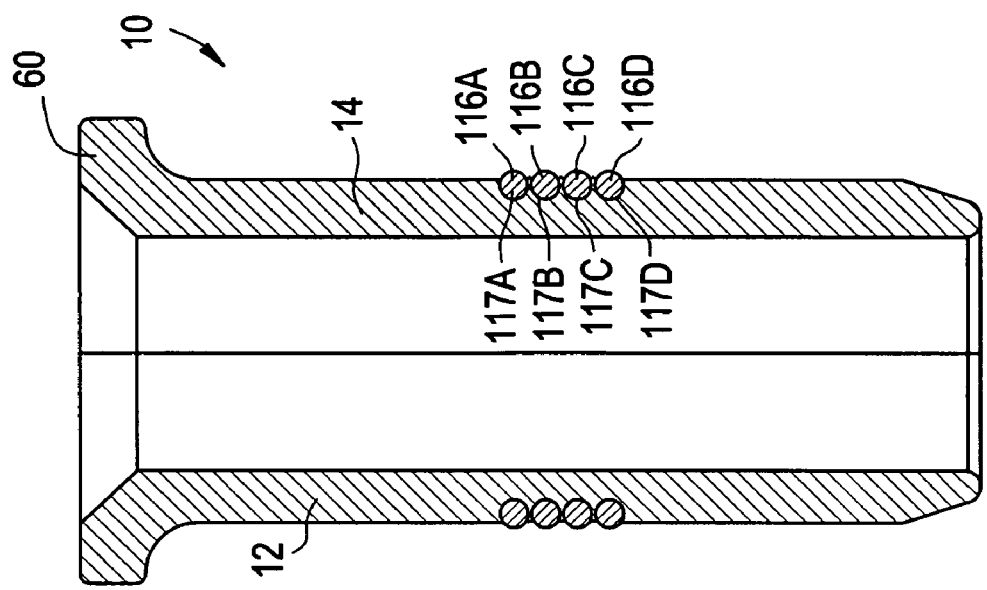
FIG. 15 is a cross sectional view of the expandable port of FIG. 13.
Figure 14:
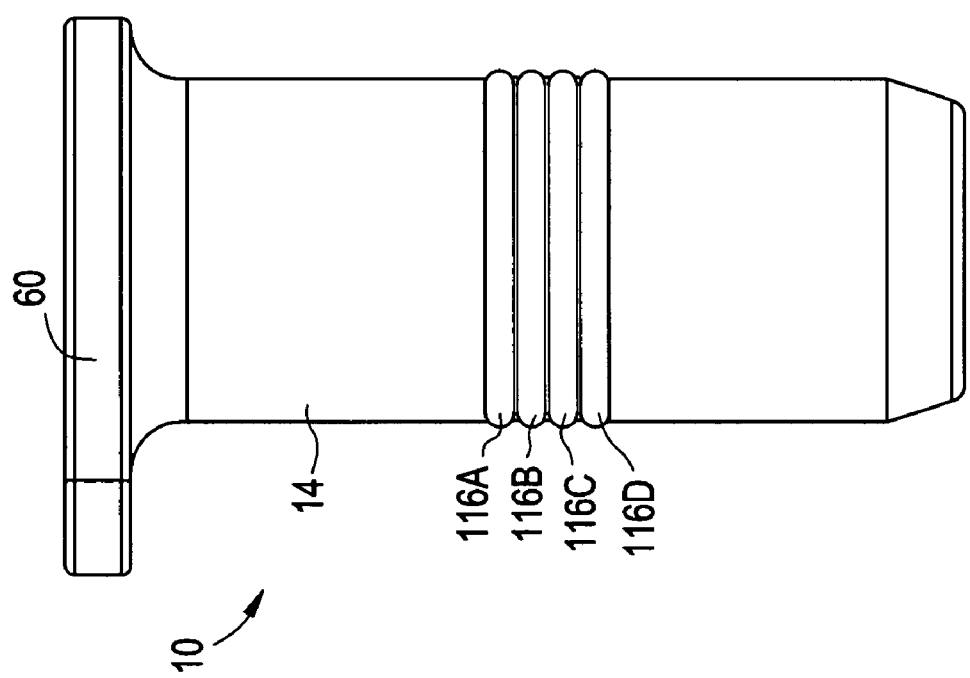
FIG. 14 is a side view of the expandable port of FIG. 13, illustrating the port in a closed position.

FIGS. 13-15 illustrate a further exemplary embodiment of an expandable port comprising a first section 12, a second section 14 and a plurality of expandable intermediate members. In the illustrated embodiment, each of the plurality of intermediate members is an elastic member 116, for example, in the form of an O-ring having a circular cross section. Each of the elastic members 116A-D may be positioned in a complementary shaped groove 117A-D provided in the outer surface of first section 12 and the second section 14 of the expandable port.

Figure 16:
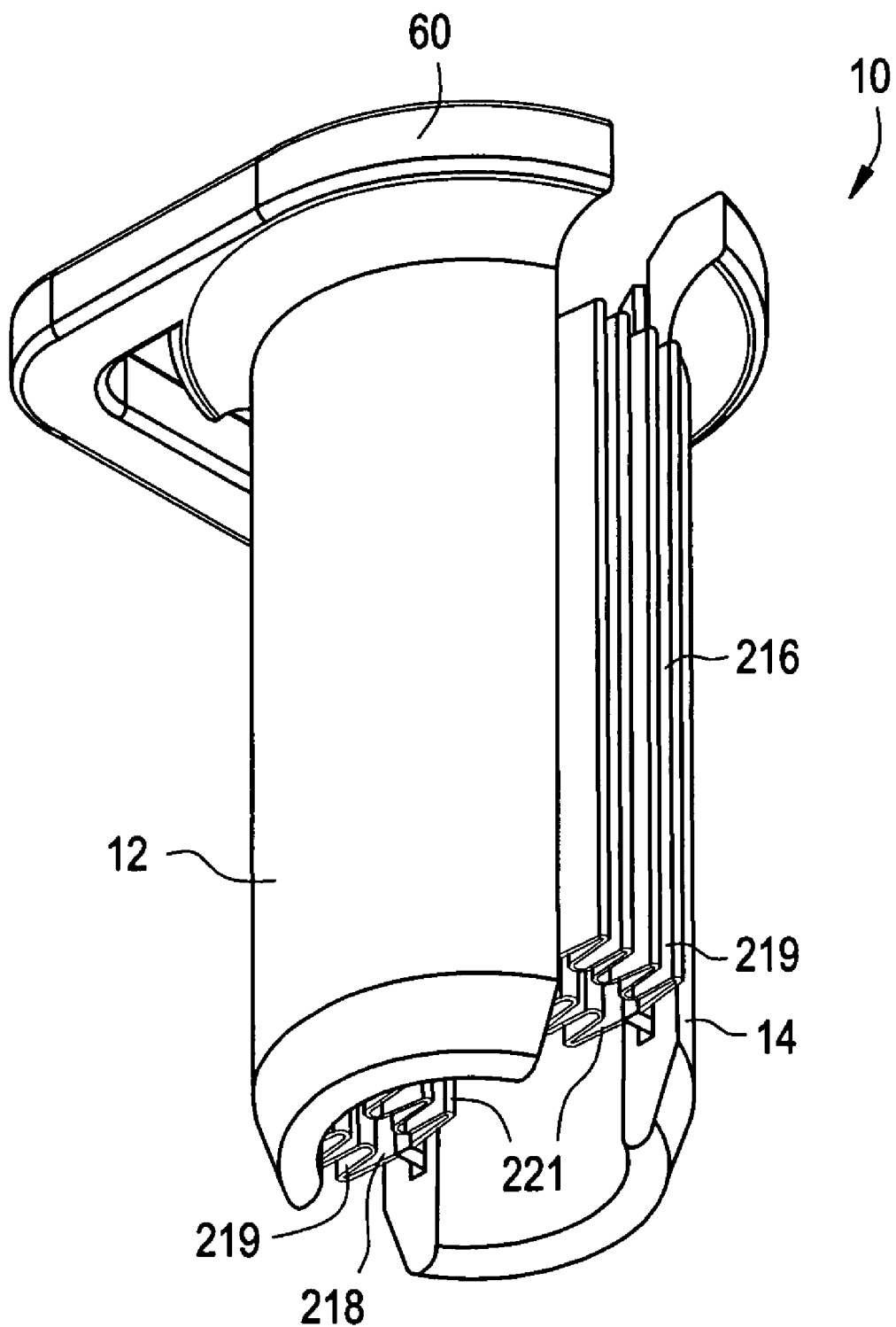
FIG. 16 is a perspective view of another exemplary embodiment of an expandable port, illustrating the port in a partially closed position.
Figure 17:
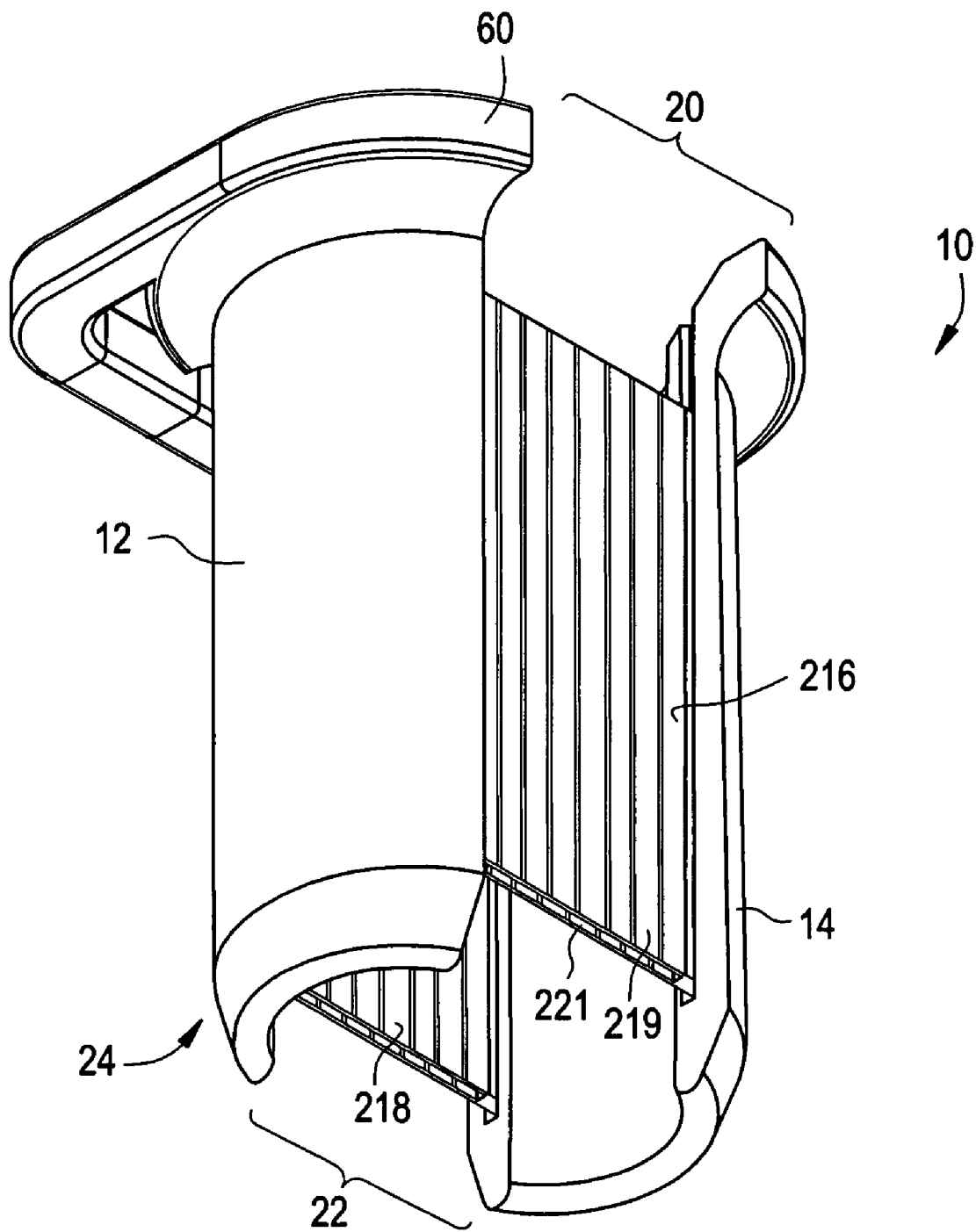
FIG. 17 is a perspective view of the expandable port of FIG. 16, illustrating the port in an expanded position.

FIGS. 16 and 17 illustrate a further exemplary embodiment of an expandable port 10 having a first section 12, a second section 14, a first intermediate section 216 and a second intermediate section 218. Each of the first intermediate section 216 and the second intermediate section 218, in the exemplary embodiment, is a bellows-like membrane that is expandable from a folded collapsed configuration to an expanded configuration, illustrated in FIG. 17. In the exemplary embodiment, the first intermediate section 216 and the second intermediate section 218 may be in the folded, collapsed configuration when the port 10 is the closed position. In the closed position, the first section 12 and the second section 14 are proximate one another, and in some embodiments, the first section 12 and the second section 14 may be in contact with one another. In those embodiments in which the first section 12 and the second section 14 contact one another, the first intermediate section 216 and the second section 218 may be positioned within housings 30, 32, 38, 40 provided in the first section 12 and the second section 14, as described above in connection with the embodiment illustrated in FIGS. 1-8. In the expanded configuration, the first intermediate section 216 spans a first gap 20 between the first section 12 and the second section 14 and the second intermediate section 218 spans a second gap 22 between the first section 12 and the second section 14.

In the illustrated embodiment, the first intermediate member 216 and the second intermediate member 218 each comprise a pair of spaced apart collapsible membranes. 219, 221. In other embodiments, a single membrane or additional membranes may be provided. One or more of the membranes 219, 221, may be connected at one edge to the first section 12 and at another end to the second section 14. The membranes 219, 221 may be constructed from any collapsible material, including, for example, polymers, fabrics, or metals, such as a sheet metal.

Figure 18:
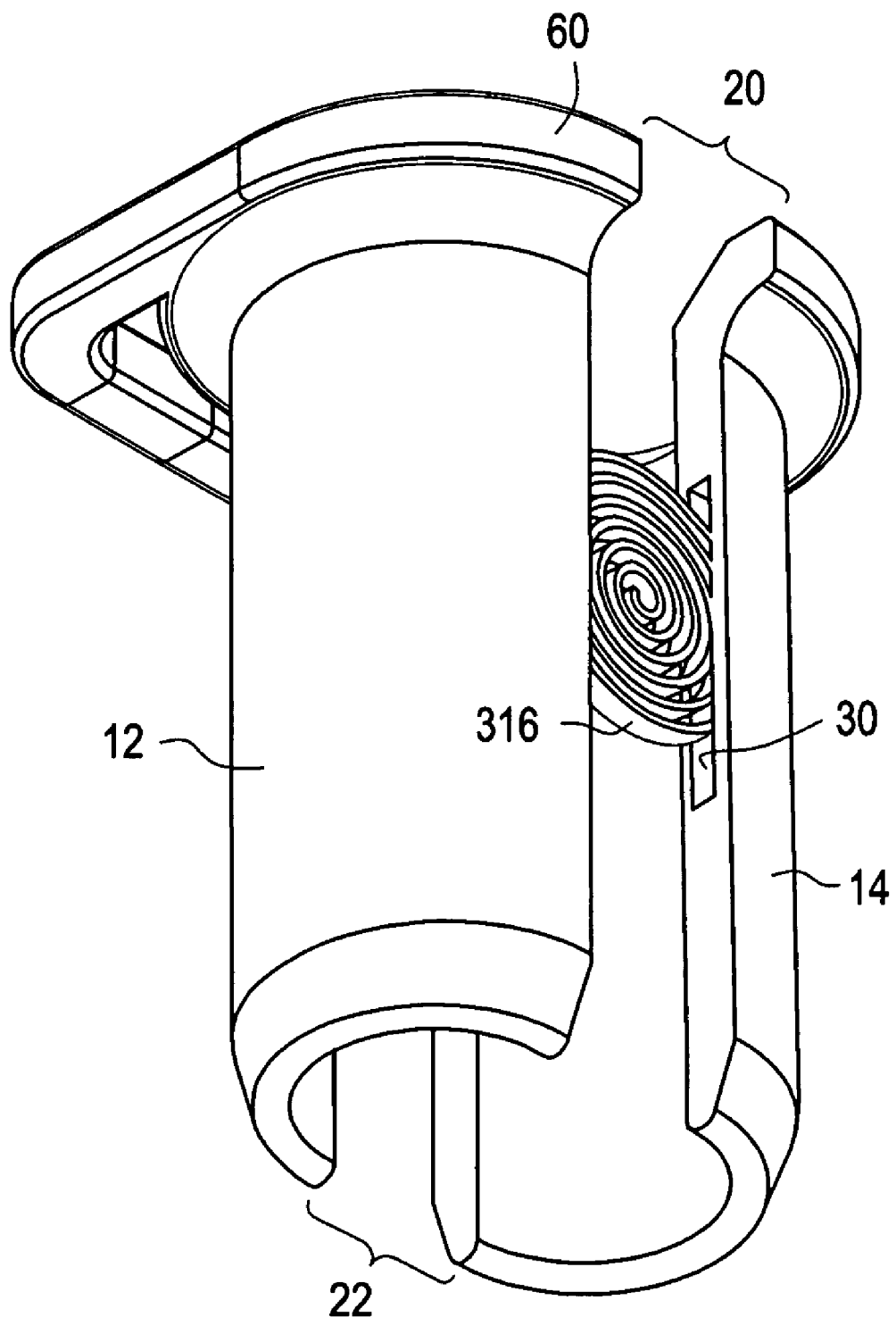
FIG. 18 is a perspective view of another exemplary embodiment of an expandable port, illustrating the port in an expanded position.
Figure 19:
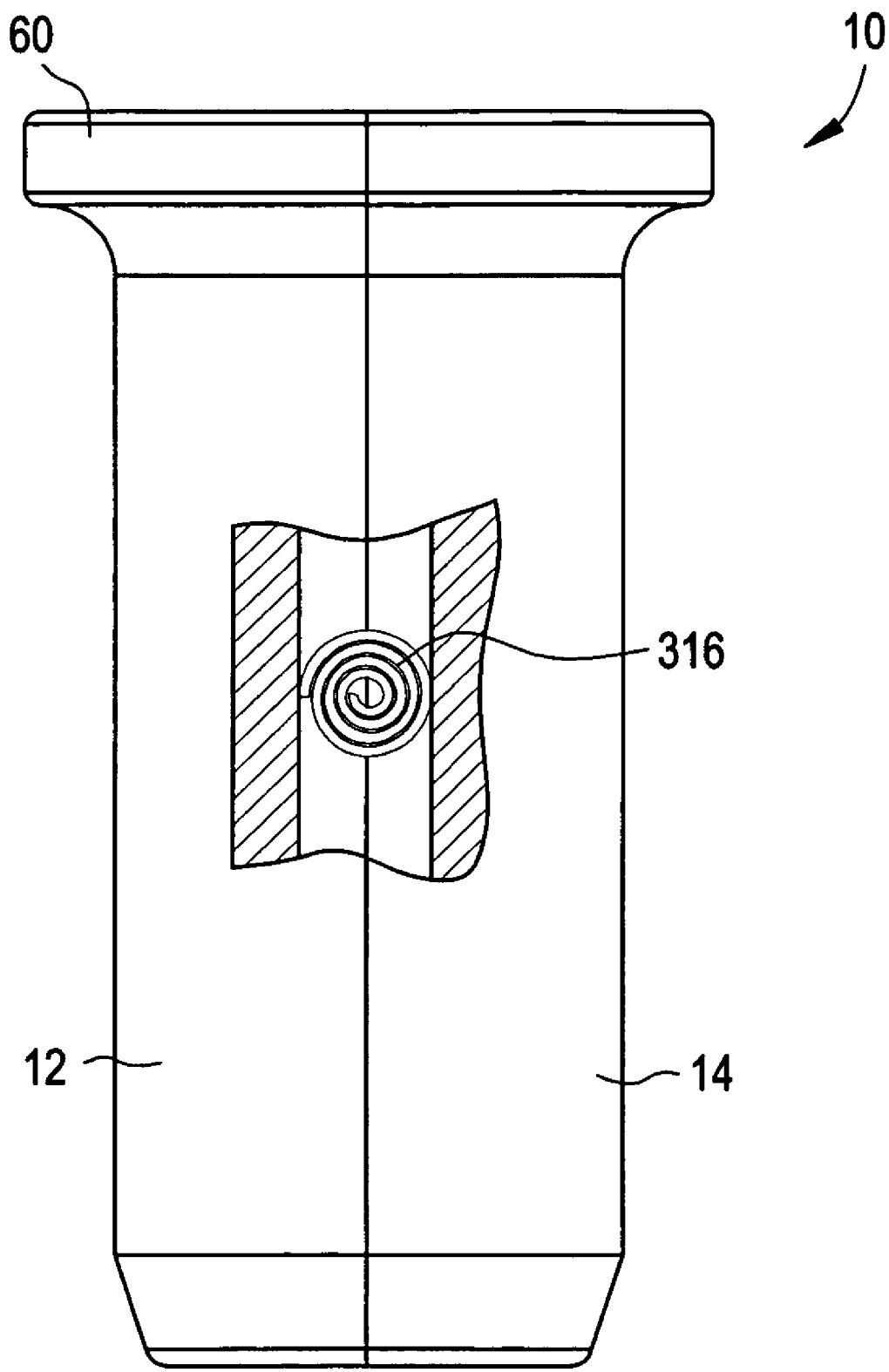
FIG. 19 is a side view of the expandable port of FIG. 18, illustrating the port in a closed position and the intermediate member in a partial cut away view.

FIGS. 18 and 19 illustrate a further exemplary embodiment of an expandable port 10 having a first section 12, a second section 14, a first intermediate section and a second intermediate section. Each of the first intermediate section and the second intermediate section, in the exemplary embodiment, is a coiled spring 316 that is expandable from a collapsed configuration, illustrated in FIG. 19, to an expanded configuration, illustrated in FIG. 18. In the exemplary embodiment, the first intermediate section and the second intermediate section may be in the collapsed configuration when the port 10 is the closed position. In the closed position, the first section 12 and the second section 14 are proximate one another, and in some embodiments including the illustrated embodiment, the first section 12 and the second section 14 may be in contact with one another. In those embodiments in which the first section 12 and the second section 14 contact one another, coiled spring 316 defining the first intermediate section and the second section may be positioned within housings 30, 32, 38, 40 provided in the first section 12 and the second section 14, as described above in connection with the embodiment illustrated in FIGS. 1-8. In the expanded configuration, the first intermediate section spans a first gap 20 between the first section 12 and the second section 14 and the second intermediate section spans a second gap 22 between the first section 12 and the second section 14. The size, shape, and material of the coiled spring 316 may be varied. For example, the spring 316 may be round (as illustrated) or elliptical; the diameter of the spring 316 may be increased to correspond to the length of the port; and the material of the spring 316 may be selected to vary the spring properties of the spring 316.

The coiled spring 316 defining the first intermediate section and the second intermediate section may bias the port 10 to the expanded position. The handle 60 may include a locking mechanism, discussed above, to lock the port in a desired configuration, for example, in the expanded position.

Figure 20:
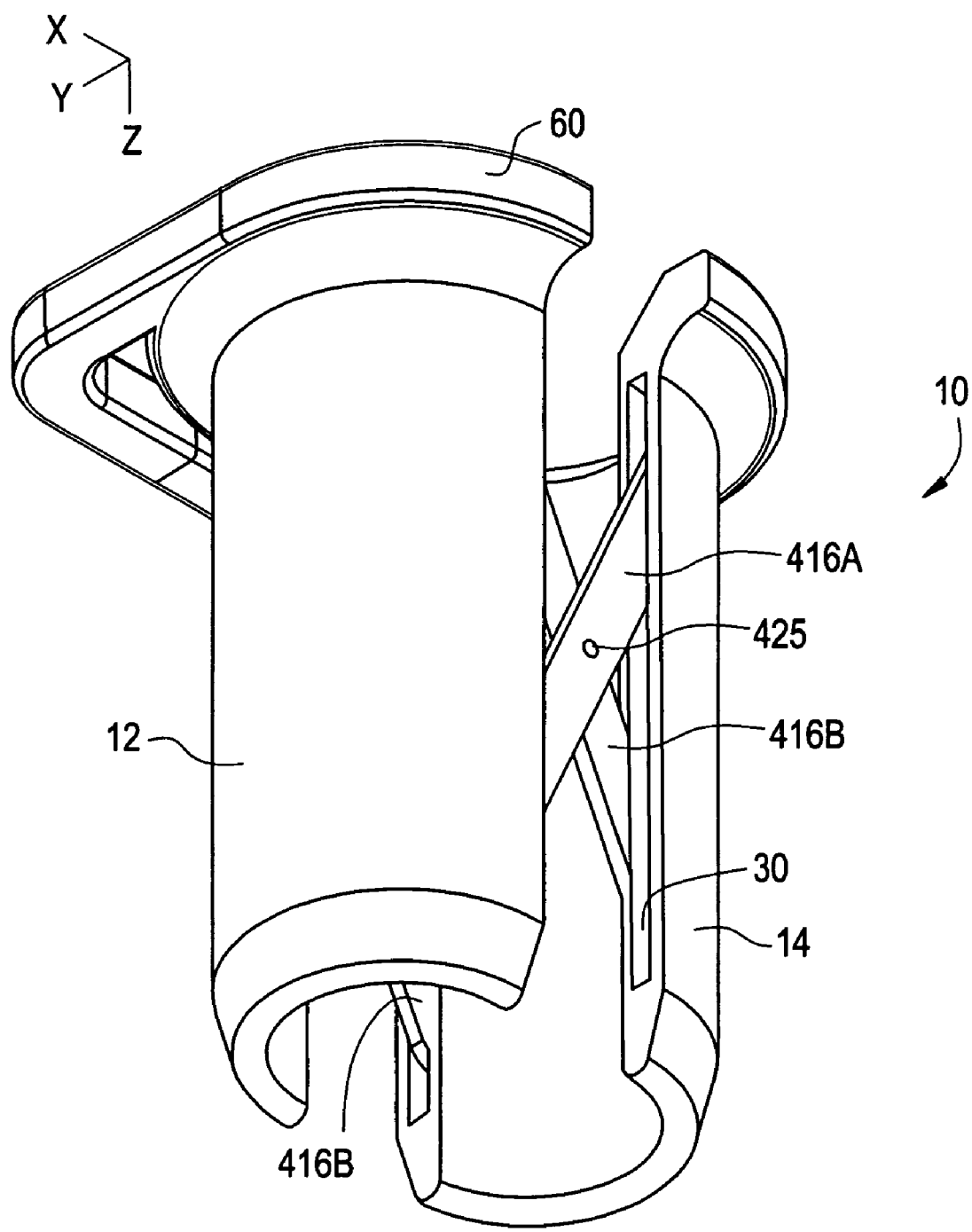
FIG. 20 is a perspective view of another exemplary embodiment of an expandable port, illustrating the port in an expanded position.
Figure 21:
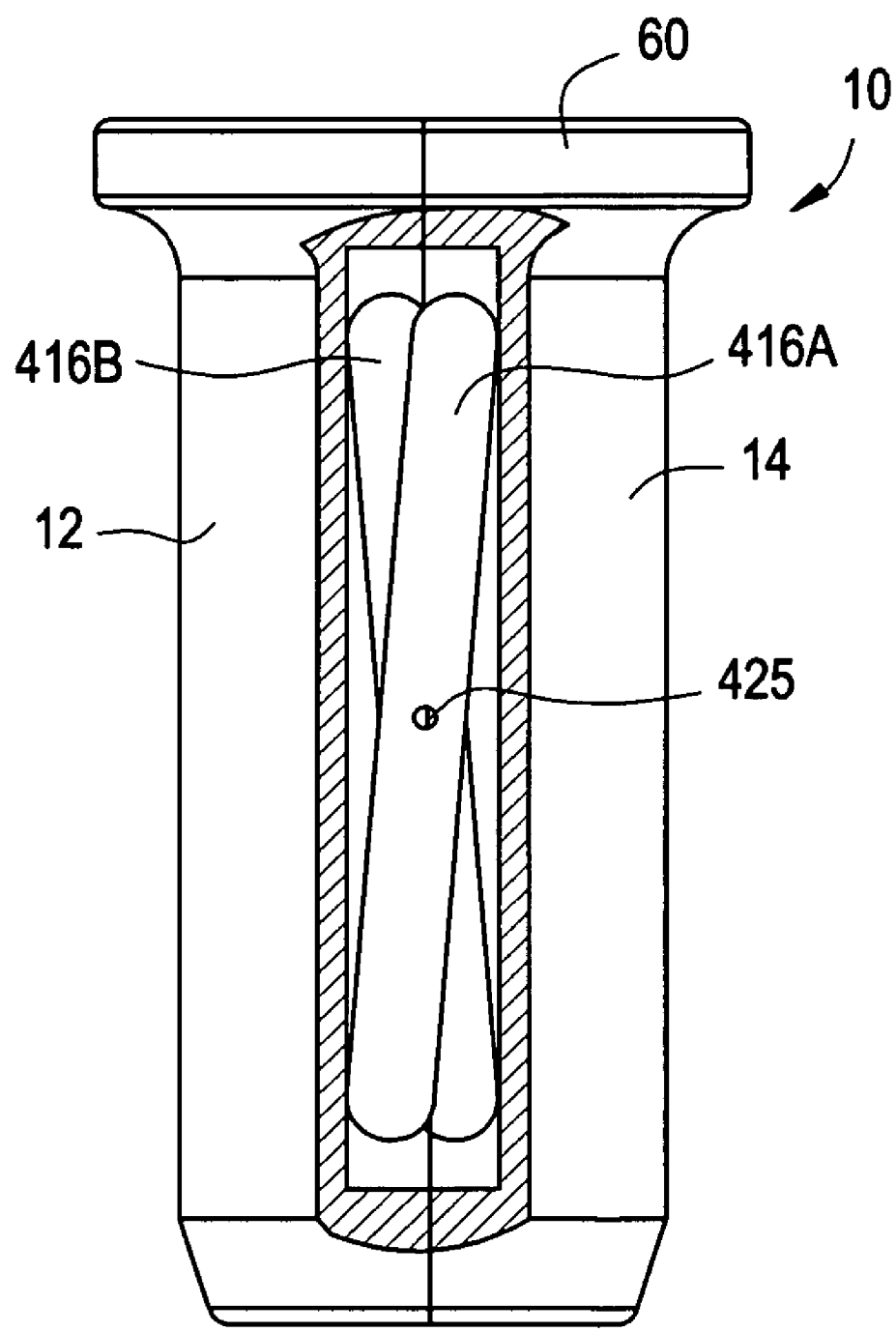
FIG. 21 is a side view of the expandable port of FIG. 20, illustrating the port in a closed position and the intermediate member in a partial cut away view.

FIGS. 20 and 21 illustrate a further exemplary embodiment of an expandable port 10 having a first section 12, a second section 14, a first intermediate section and a second intermediate section. Each of the first intermediate section and the second intermediate section, in the exemplary embodiment, comprise a pair of interconnected arms 416A,B that are expandable from a collapsed configuration, illustrated in FIG. 21, to an expanded configuration, illustrated in FIG. 20. The arms 416A, 416B are connected to one another by a pivot pin 425. The arms 416A, 416B may pivot about a pivot axis defined by the pivot pin 425 between the collapsed position and the expanded configuration. A spring, e.g., a torsion spring, may be provided to bias the arms 416A, 416B to the expanded configuration. The arms 416A, 416B may be positioned in housings 30, 32, 38, 40 provided in the first section 12 and the second section 14. In the illustrated embodiment, each of the arms 416A, 416B may contact at one end the first section 12 and may contact at another end the second section 14.

In certain exemplary embodiments, the arms 416A, 416B may be configured to expand as the expandable port 10 is expanded. In alternative embodiments, the arms 416A, 416B may be expanded manually by, for example, an instrument.

Figure 22:
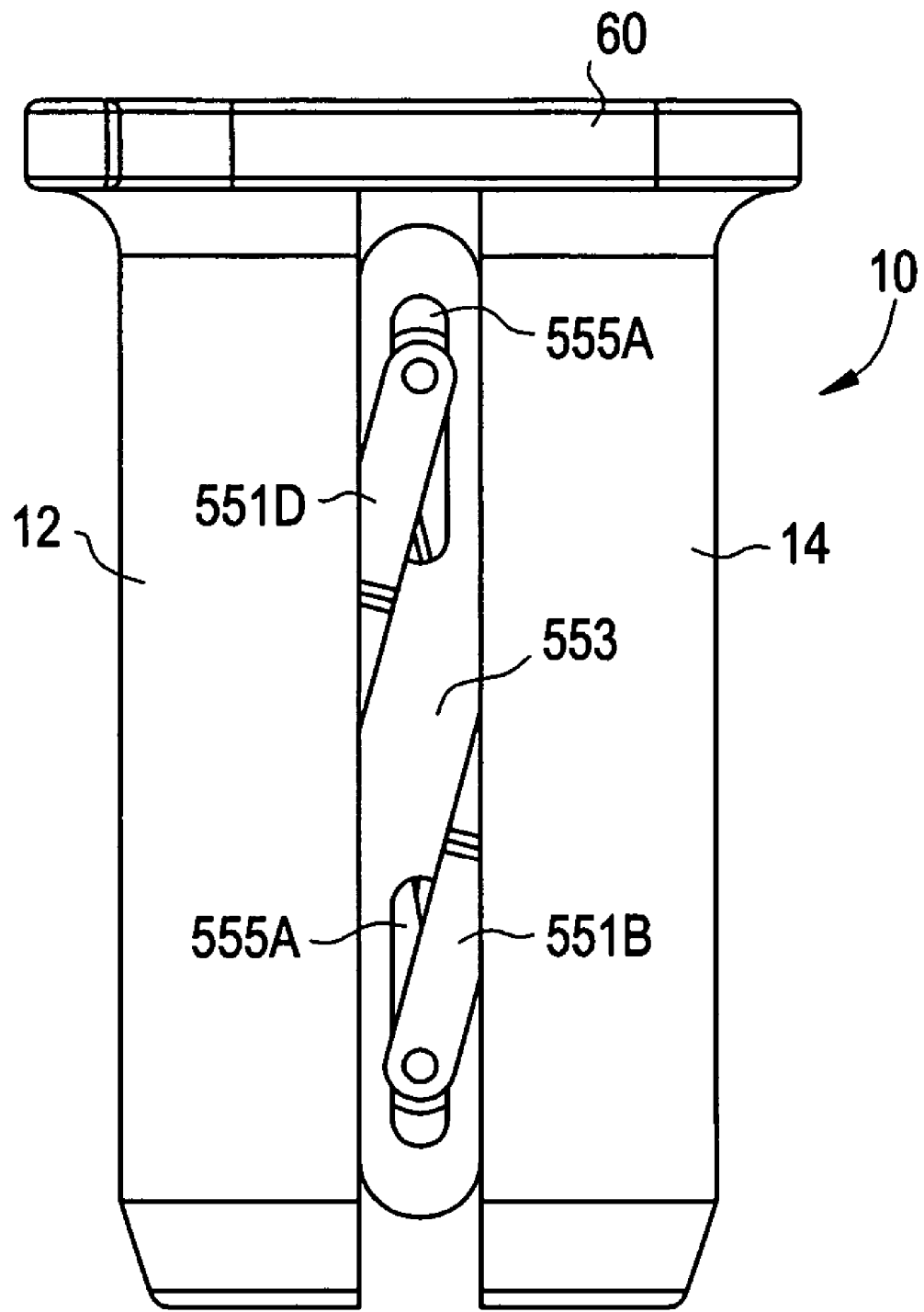
FIG. 22 is a side view of another exemplary embodiment of an expandable port, illustrating the port in a partially closed position.
Figure 23:
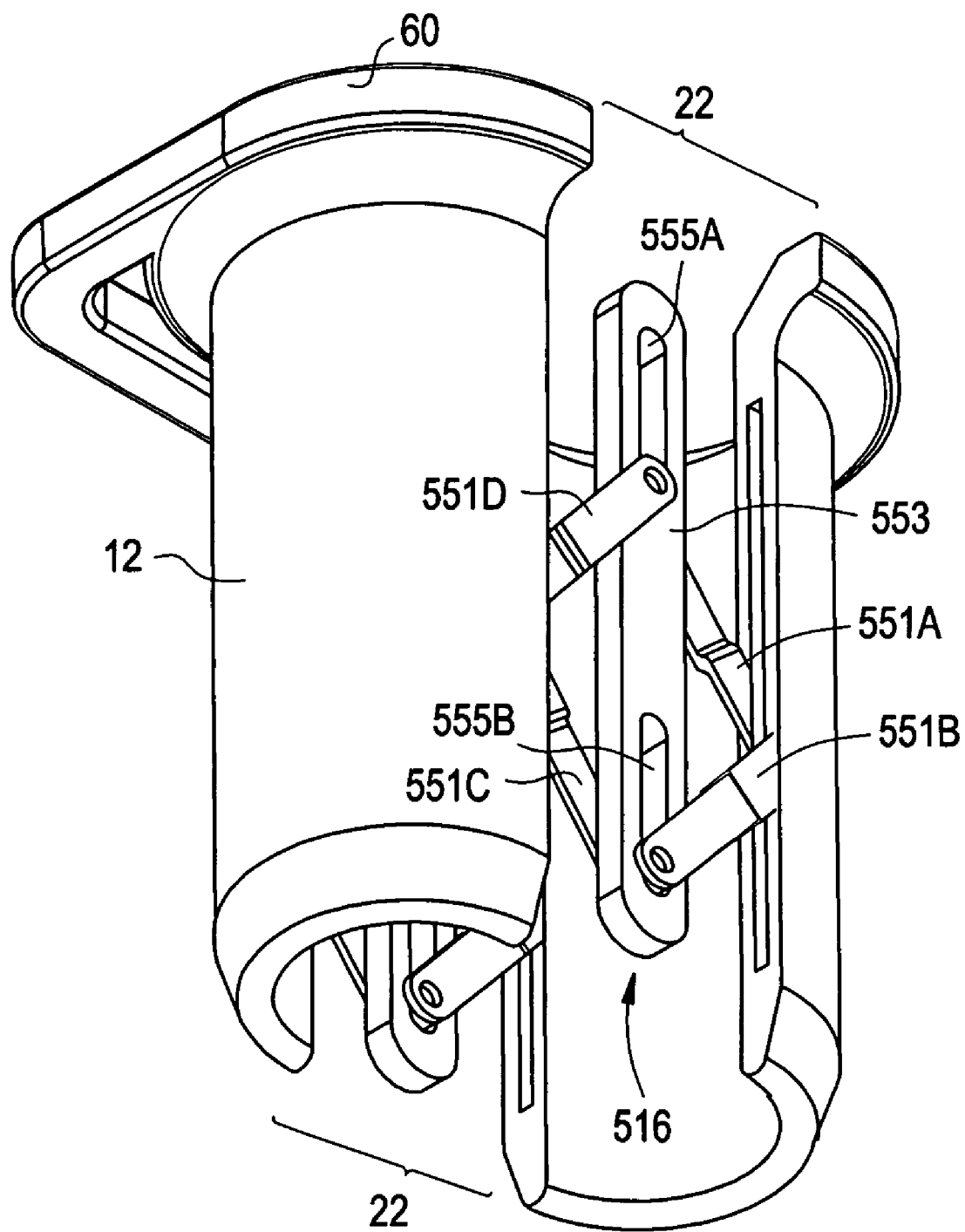
FIG. 23 is a perspective view of the expandable port of FIG. 22, illustrating the port in an expanded position.

FIGS. 22 and 23 illustrate a further exemplary embodiment of an expandable port 10 having a first section 12, a second section 14, a first intermediate section and a second intermediate section. Each of the first intermediate section and the second intermediate section, in the exemplary embodiment, comprises a linkage 516 that is expandable from a partially collapsed configuration, illustrated in FIG. 22, to an expanded configuration, illustrated in FIG. 23. The linkage 516 includes a four links 551A-D each connected to a central link 553. First link 551A is connected at one end to the second section 14 and at another end to the central link 553. Second link 551B is connected at one end to the second section 14 and at another end to the central link 553. Third link 551C is connected at one end to the first section 12 and at another end to the central link 553. Fourth link 551D is connected at one end to the first section 12 and at another end to the central link 553. First link 551A and fourth link 551D may move relative to the central link 553 by translating along a first slot 555A. Second link 551B and third link 551C may move relative to the central link 553 by translating along a second slot 555B. Motion of the links 551A-D relative to the central link 553 allows the linkage to expand from a collapsed configuration to an expanded configuration. The links 551A-D may be positioned in housings 30, 32, 38, 40 provided in the first section 12 and the second section 14.

In certain exemplary embodiments, the linkage 516 may be configured to expand as the expandable port 10 is expanded. In alternative embodiments, the linkage 516 may be expanded manually by, for example, an instrument.

Figure 24:
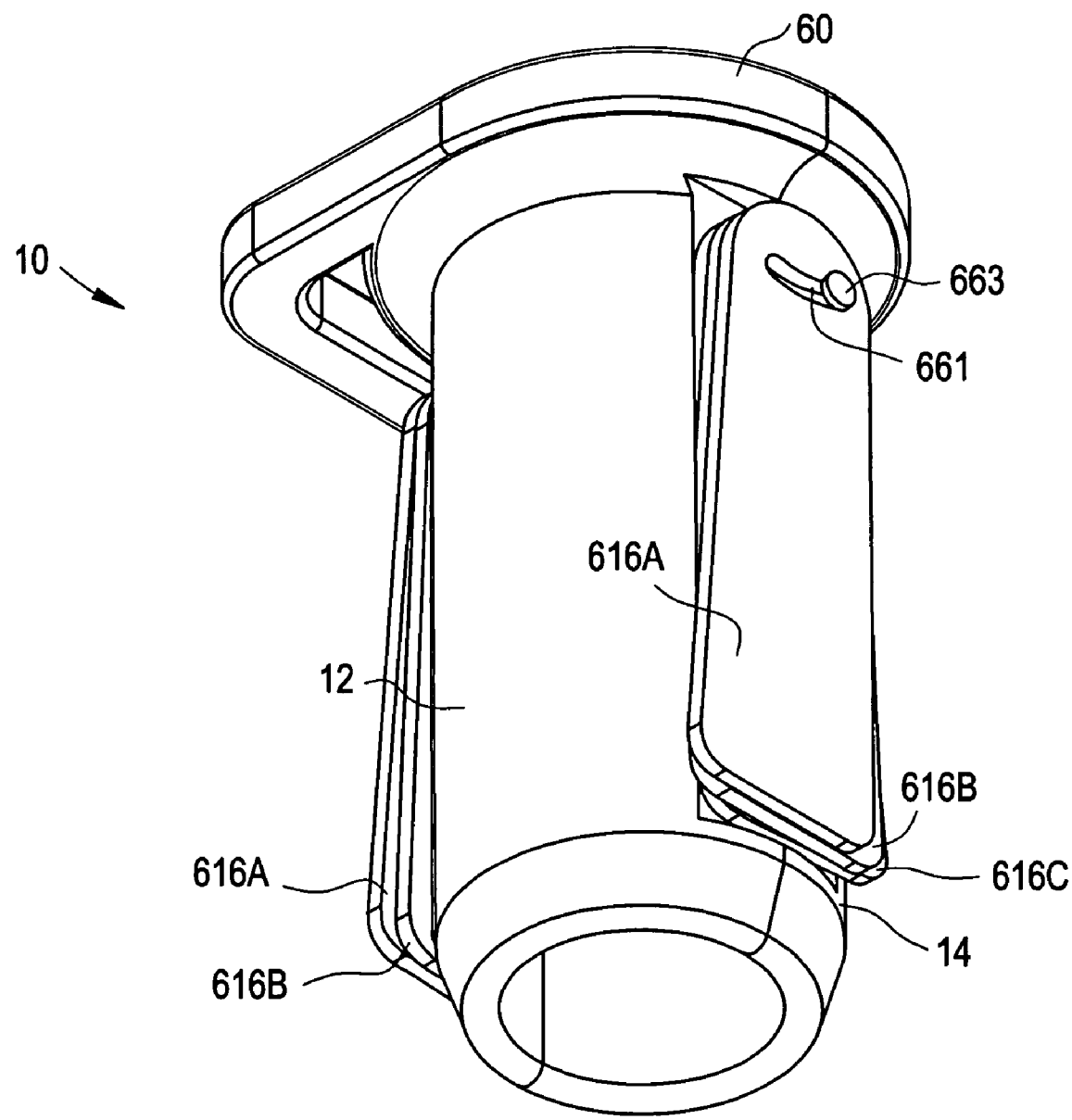
FIG. 24 is a perspective view of another exemplary embodiment of an expandable port, illustrating the port in a closed position.
Figure 25:
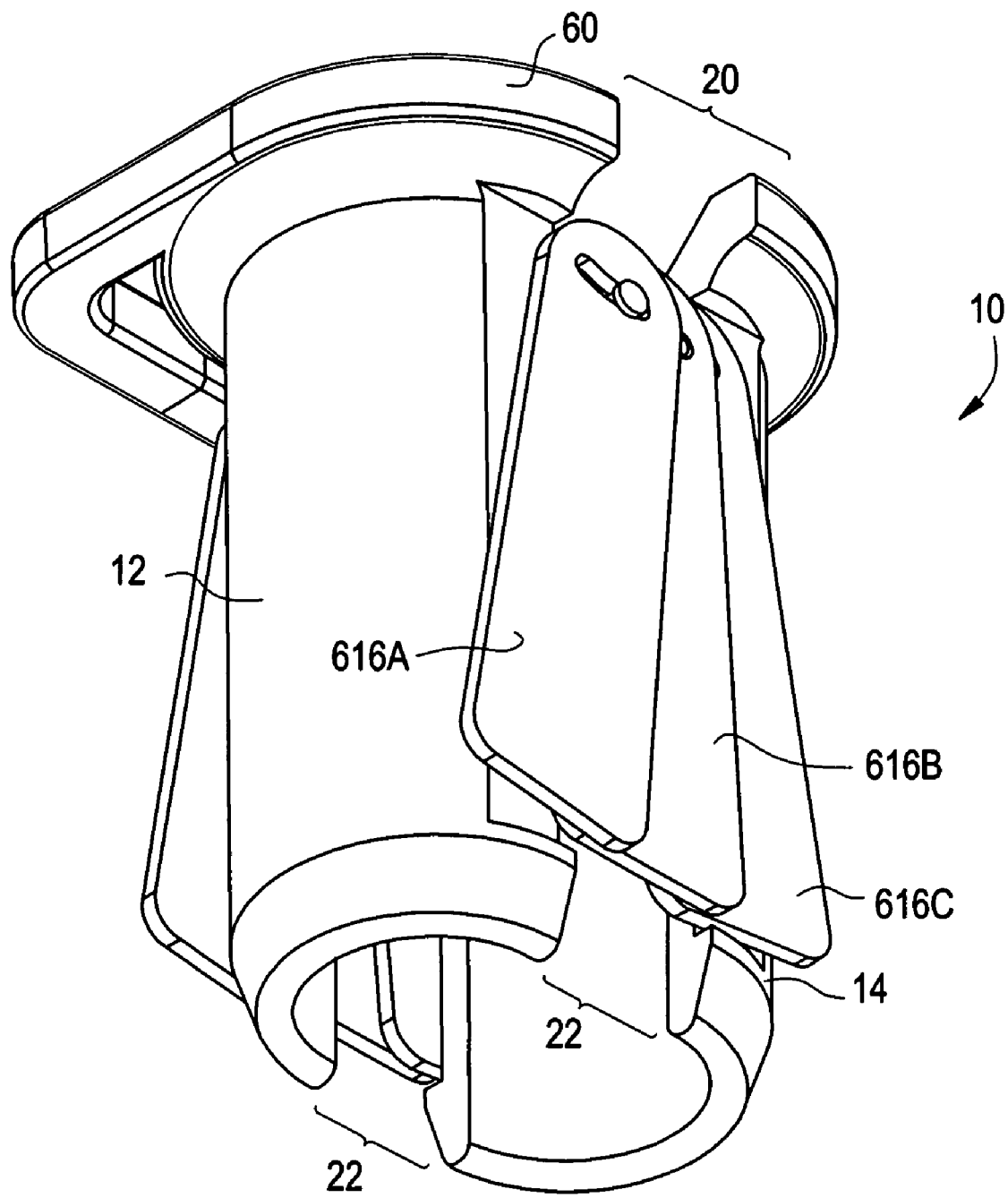
FIG. 25 is a perspective view of the expandable port of FIG. 24, illustrating the expandable port in an expanded position.

FIGS. 24 and 25 illustrate a further exemplary embodiment of an expandable port 10 having a first section 12, a second section 14, a first intermediate section and a second intermediate section. Each of the first intermediate section and the second intermediate section, in the exemplary embodiment, comprises a plurality of blades 616A-C that are expandable from a collapsed, generally overlapping configuration, illustrated in FIG. 24, to an expanded, generally spread configuration, illustrated in FIG. 25. In the illustrated embodiment, three blades 616 are provided, however, any number of blades may be provided. In the illustrated embodiment, the blades 616A-C may include a slot 661 for receiving a retaining pin 663. Moving the blades 616A-C relative to one another and relative to the retaining pin 663 may expand the blades 616A-C. In the exemplary embodiment, the blades 616A-C expand in the manner of a fan, with the distal ends of the blades moving a greater distance than the proximal end of the blades. The blades 616 may be connected to the outer surface of the first section 12 and the second section 14, as in the illustrated embodiment or, alternatively, the blades 616 may be positioned in housings 30, 32, 38, 40 provided in the first section 12 and the second section 14.

Figure 28:
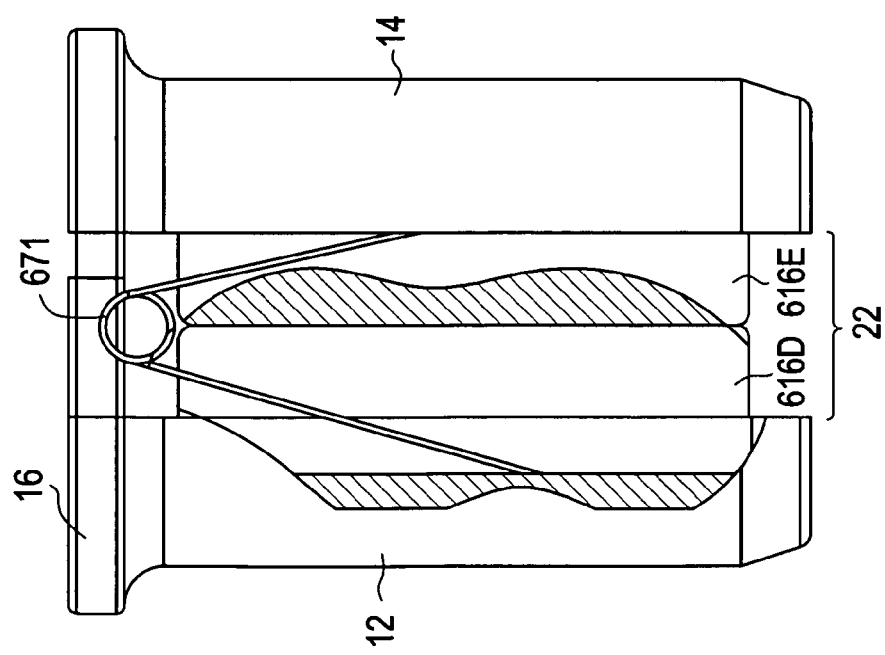
FIG. 28 is a side view of the expandable port of FIG. 26, illustrating the port in an expanded position and intermediate member in a partial cut away view.

FIGS. 26-28 illustrate a further exemplary embodiment of an expandable port 10 having a first section 12, a second section 14, a first intermediate section and a second intermediate section. Each of the first intermediate section and the second intermediate section, in the exemplary embodiment, comprises a plurality of blades 616D,E that are expandable from a collapsed, generally overlapping configuration, illustrated in FIG. 26, to an expanded, generally spread configuration, illustrated in FIGS. 27-28. The blades 616 may be positioned in housings 30, 32, 38, 40 provided in the first section 12 and the second section 14. In contrast to the embodiment illustrated in FIGS. 24 and 25, the blades 616D,E expand laterally to span the gaps 20, 22 between the first section 12 and the second section 14 when the port 10 is expanded. One or more springs 671 may be provided to bias the port 10 to an expanded configuration. The spring 671 may be a torsion spring having elongated arms that may be positioned in housings 30, 32, 38, 40 provided in the first section 12 and the second section 14.

Figure 29:
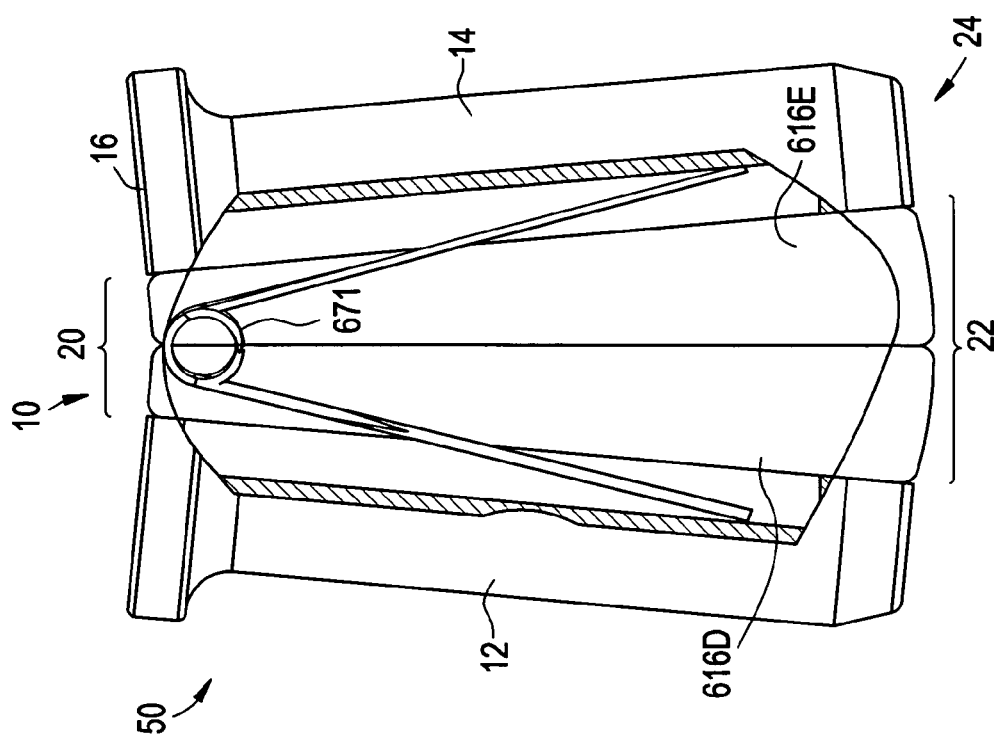
FIG. 29 is a side view of an alternative embodiment of the expandable port of FIG. 26, illustrating the port in an expanded position and the intermediate member in a partial cut away view.

In certain exemplary embodiments, expandable port may expand laterally and pivotally. Referring to FIG. 29, for example, the exemplary port 10 includes a first section 12, a second section 14, a first intermediate section in the form of blade 616D and a second intermediate section in the form of blade 616E. As the port 10 expands to an expanded configuration, as illustrated in FIG. 29, the first section 12 and the second section 14 move laterally and pivotally with respect to each other. As a result, the distal end 24 of the port 10 may expanded a distance greater than the proximal end 50 of the port 10 such that distal gap 22 is greater than proximal gap 20.

In certain exemplary embodiments, the blades 616A-E may be configured to expand as the expandable port 10 is expanded. In alternative embodiments, the plurality of blades 616A-E may be expanded manually by, for example, an instrument.

Figure 31:
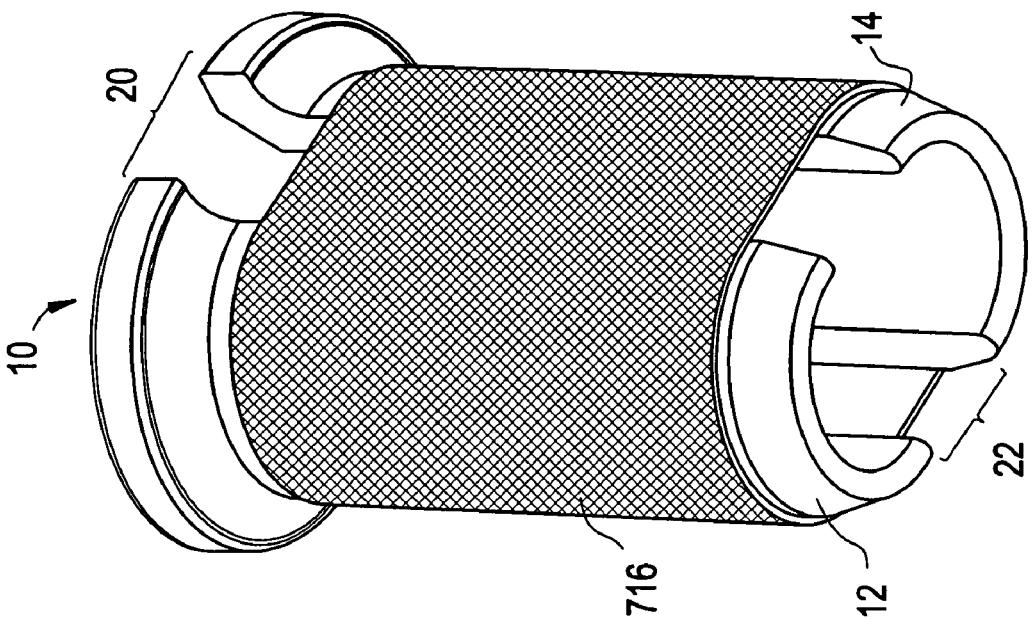
FIG. 31 is a perspective view of the expandable port of FIG. 30, illustrating the port in an expanded configuration.
Figure 30:
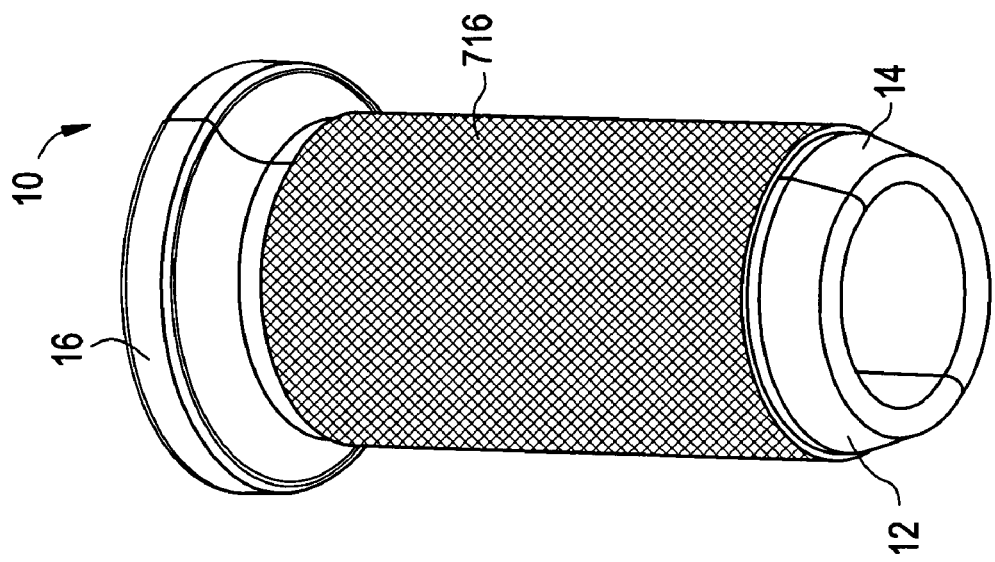
FIG. 30 is a perspective view of another exemplary embodiment of an expandable port, illustrating the port in a closed position.

FIGS. 30 and 31 illustrate another exemplary embodiment of an expandable port 10 having a first section 12, a second section 14, and at least one expandable intermediate section. In the illustrated embodiment, the expandable intermediate section is a sheath 716 positioned about the outer surface of the port 10 that is expandable from a collapsed configuration, illustrated in FIG. 30 to an expanded configuration, illustrated in FIG. 31, to span the gaps 20 and 22 between the first section 12 and the second section 14. The sheath 716 may have a shape corresponding to the cross sectional shape of the port 10. For example, the sheath 716 may be generally circular or generally oval in shape. The sheath 716 may be constructed of a polymer, a fabric, a composite thereof or any other suitable material. In certain embodiments, the sheath 716 may be constructed from an elastic material, such as natural and synthetic polymers, such as, for example, rubber, to bias the port 10 to a closed configuration.

The length of the sheath 716 and the position of the sheath 716 along the length of the port 10 may be varied. In the illustrated embodiment, for example, the length of the sheath 716 is approximately equal to the length of the first section 12 and the second section 14. In other embodiments, the sheath 716 may have a length less than the length of the first section 12 and/or second section 14. In such exemplary embodiments, the sheath 716 may be centrally located, or may be located approximate to the distal end 24 of the port 10 or approximate the proximal end of the port 10.

One skilled in the art will appreciate that the size, e.g., width, length and thickness, the number, and the location relative to the port of the exemplary intermediate sections described above in connection with the embodiments of FIGS. 1-30 may be varied.

While the expandable ports and methods of minimally invasive surgery of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

The invention claimed is:

1. An expandable port for minimally invasive surgery, the port comprising:

a first section having a proximal end, a distal end, a first side, and a second side, the first section being arcuate in shape, the first side and the second side each extending from the proximal end to distal end of the first section, the first section have an inner wall and a coextensive outer wall each of which extend continuously from the proximal end to the distal end of the first section in a parallel arrangement, the inner wall connecting to the outer wall at the distal end of the first section along the extent of the distal end of the first section, the inner wall being spaced apart from the outer wall at two separate and distinct locations to define two separate and distinct housings, the two housings comprising a first housing opening at the first side of the first section and a second housing opening at the second side of the first section;

a second section having a proximal end, a distal end, a first side, and a second side, the second section being arcuate in shape, the first side and the second side each extending from the proximal end to distal end of the first section, the second section have an inner wall and a coextensive outer wall each of which extend continuously from the proximal end to the distal end of the second section in a parallel arrangement, the inner wall connecting to the outer wall at the distal end of the second section along the extent of the distal end of the second section, the inner wall being spaced apart from the outer wall at two separate and distinct locations to define two separate and distinct housings, the two housings comprising a third housing opening at the first side of the second section and a fourth housing opening at the second side of the second section;

a first intermediate section having a length approximate to a length of the first section and a length of the second section, a second intermediate section having a length approximate to a length of the first section and a length of the second section;

the port being expandable from a closed configuration in which the first side of the first section engages the first side of the second section along the length of the first section and length of the second section and the second side of the first section engages the second side of the second section along the length of the first section and the length of the second section to an expanded configuration in which the first side of the first section is spaced apart from the first side of the second section to create a first gap therebetween and the second side of the first section is space apart from the second side of the second section to define a second gap therebetween, wherein when the port is in the closed configuration a first portion of the first intermediate section is positioned within the first housing and a second portion of the first intermediate section is positioned in the third housing and a first portion of the second intermediate section is positioned within the second housing and a second portion of the second intermediate section is positioned in the fourth housing, and wherein when the port is in the expanded configuration the first intermediate section spans the first gap between the first side of the first section and the first side of the second section and the second intermediate section spans the second gap between the second side of the first section and the second side of the second section, the inner wall of the first section, the inner wall of the second section, the first intermediate section, and the second section providing a continuous uninterrupted pathway from the proximal ends of the first section and the second section to the distal ends of the first section and the second section when the port is in the expanded configuration.

2. The expandable port of claim 1, wherein the port is generally circular in cross-section in the closed configuration.

3. The expandable port of claim 1, wherein the port is generally oval in cross-section in the closed configuration.

4. The expandable port of claim 1, wherein the first housing opens at the proximal end of the first section, the second housing opens at the proximal end of the first section, the third housing opening at the proximal end of the second section, and the fourth housing opens at the proximal end of the second section.

* * * * *